(12) United States Patent
Sutherland et al.

(10) Patent No.: US 11,484,379 B2
(45) Date of Patent: Nov. 1, 2022

(54) MICROSURGERY-SPECIFIC HAPTIC HAND CONTROLLER

(71) Applicant: OrbSurgical Ltd., Calgary (CA)

(72) Inventors: Garnette Roy Sutherland, Calgary (CA); Hamidreza Hoshyarmanesh, Calgary (CA); Kourosh Zareinia, Calgary (CA); Sanju Lama, Calgary (CA)

(73) Assignee: ORBSURGICAL LTD., Calgary (CA)

( * ) Notice: Subject to any disclaimer, the term of this patent is extended or adjusted under 35 U.S.C. 154(b) by 304 days.

(21) Appl. No.: 16/958,016

(22) PCT Filed: Dec. 28, 2018

(86) PCT No.: PCT/CA2018/000243
§ 371 (c)(1),
(2) Date: Jun. 25, 2020

(87) PCT Pub. No.: WO2019/126863
PCT Pub. Date: Jul. 4, 2019

(65) Prior Publication Data
US 2021/0059780 A1    Mar. 4, 2021

Related U.S. Application Data

(60) Provisional application No. 62/611,024, filed on Dec. 28, 2017.

(51) Int. Cl.
*G09G 5/00* (2006.01)
*A61B 34/00* (2016.01)
(Continued)

(52) U.S. Cl.
CPC .............. *A61B 34/76* (2016.02); *A61B 34/37* (2016.02); *A61B 34/74* (2016.02); *A61B 90/90* (2016.02); *B25J 3/04* (2013.01)

(58) Field of Classification Search
CPC combination set(s) only.
See application file for complete search history.

(56) References Cited

U.S. PATENT DOCUMENTS

| 2,475,484 A | 7/1949 | De Nise |
| 4,062,455 A | 12/1977 | Flatau |

(Continued)

FOREIGN PATENT DOCUMENTS

| WO | 0184530 A1 | 11/2001 |
| WO | 2007068050 A1 | 6/2007 |

(Continued)

OTHER PUBLICATIONS

Adachi., "Touch and Trace on the Free-form Surface of Virtual Object," Proceedings of IEEE Virtual Reality Annual International Symposium, Sep. 1993, pp. 162-168.

(Continued)

*Primary Examiner* — Insa Sadio
(74) *Attorney, Agent, or Firm* — Borden Ladner Gervais LLP; Curtis B. Behmann

(57) ABSTRACT

A local haptic hand controller is provided for enabling an operator to remotely perform fine manipulation, such as microsurgery, in conjunction with a remotely located robotic manipulator, for example at which the microsurgery is to be performed. The local haptic hand controller includes a base, a kinematic structure in communication with the base and comprises a gimbal as an end effector. A local surgical tool is provided at the gimbal and has a shape and construction substantially similar to a remote surgical tool provided at the remote robotic manipulator. A control system is in communication with the local surgical tool and with the remote surgical tool, and configured to enable operation of the local haptic hand controller when a local surgical tool identifier matches a remote surgical tool identifier.

20 Claims, 19 Drawing Sheets

(51) Int. Cl.
*A61B 34/37* (2016.01)
*A61B 90/90* (2016.01)
*B25J 3/04* (2006.01)

(56) References Cited

U.S. PATENT DOCUMENTS

| | | |
|---|---|---|
| 4,555,960 A | 12/1985 | King |
| 4,648,782 A | 3/1987 | Kraft |
| 4,721,274 A | 1/1988 | Erb |
| 4,895,039 A | 1/1990 | Hegg |
| 4,913,000 A | 4/1990 | Wyllie |
| 4,914,976 A | 4/1990 | Wyllie |
| 4,988,981 A | 1/1991 | Zimmerman et al. |
| 5,007,300 A | 4/1991 | Siva |
| 5,019,761 A | 5/1991 | Kraft |
| 5,024,116 A | 6/1991 | Kraft |
| 5,103,404 A | 4/1992 | McIntosh |
| 5,142,931 A | 9/1992 | Menahem |
| 5,143,505 A | 9/1992 | Burdea et al. |
| 5,149,270 A | 9/1992 | McKeown |
| 5,184,319 A | 2/1993 | Kramer |
| 5,193,963 A | 3/1993 | McAffee et al. |
| 5,255,211 A | 10/1993 | Redmond |
| 5,264,768 A | 11/1993 | Gregory et al. |
| 5,266,875 A | 11/1993 | Slotine et al. |
| 5,350,033 A | 9/1994 | Kraft |
| 5,354,162 A | 10/1994 | Burdea et al. |
| 5,382,885 A | 1/1995 | Salcudean et al. |
| 5,403,191 A | 4/1995 | Tuason |
| 5,459,382 A | 10/1995 | Jacobus et al. |
| 5,478,344 A | 12/1995 | Stone et al. |
| 5,478,345 A | 12/1995 | Stone et al. |
| 5,480,406 A | 1/1996 | Nolan et al. |
| 5,503,149 A | 4/1996 | Beavin |
| 5,589,828 A | 12/1996 | Armstrong |
| 5,589,854 A | 12/1996 | Tsai |
| 5,625,576 A | 4/1997 | Massie et al. |
| 5,643,087 A | 7/1997 | Marcus et al. |
| 5,706,027 A | 1/1998 | Hilton et al. |
| 5,724,068 A | 3/1998 | Sanchez et al. |
| 5,742,278 A | 4/1998 | Chen et al. |
| 5,766,016 A | 6/1998 | Sinclair et al. |
| 5,800,179 A | 9/1998 | Bailey |
| 6,038,488 A | 3/2000 | Barnes et al. |
| 6,062,865 A | 5/2000 | Bailey |
| 6,088,020 A | 7/2000 | Mor |
| 6,104,382 A | 8/2000 | Martin et al. |
| 6,113,395 A | 9/2000 | Hon |
| 6,154,198 A | 11/2000 | Rosenberg |
| 6,307,486 B1 | 10/2001 | Takeda et al. |
| 6,369,834 B1 | 4/2002 | Zilles et al. |
| 6,377,011 B1 | 4/2002 | Ben-Ur |
| 6,396,232 B2 | 5/2002 | Haan et al. |
| 6,417,638 B1 | 7/2002 | Guy et al. |
| 6,529,183 B1 | 3/2003 | MacLean et al. |
| 6,697,043 B1 | 2/2004 | Shahoian |
| 6,810,281 B2 | 10/2004 | Brock et al. |
| 6,857,878 B1 | 2/2005 | Chosack et al. |
| 6,863,536 B1 | 3/2005 | Fisher et al. |
| 6,924,787 B2 | 8/2005 | Kramer et al. |
| 6,939,138 B2 | 9/2005 | Chosack et al. |
| 6,985,133 B1 | 1/2006 | Rodomista et al. |
| 6,991,627 B2 | 1/2006 | Madhani et al. |
| 7,023,423 B2 | 4/2006 | Rosenberg |
| 7,056,123 B2 | 6/2006 | Gregorio et al. |
| 7,236,618 B1 | 6/2007 | Chui et al. |
| 7,261,565 B2 | 8/2007 | Chosack et al. |
| 7,289,106 B2 | 10/2007 | Bailey et al. |
| 8,716,973 B1 * | 5/2014 | Lammertse ............ G06F 3/016 345/184 |
| 8,834,170 B2 | 9/2014 | Kurenov et al. |
| 8,862,268 B2 | 10/2014 | Robinson et al. |
| 9,652,591 B2 * | 5/2017 | Moctezuma de la Barrera .......... A61B 17/154 |
| 2002/0126036 A1 | 9/2002 | Flaherty et al. |
| 2003/0210259 A1 | 11/2003 | Liu et al. |
| 2005/0080403 A1 | 4/2005 | Takahashi |
| 2005/0118557 A1 | 6/2005 | Sumner, II et al. |
| 2005/0142525 A1 | 6/2005 | Cotin et al. |
| 2005/0181340 A1 | 8/2005 | Haluck |
| 2005/0214727 A1 | 9/2005 | Stoianovici et al. |
| 2005/0221263 A1 | 10/2005 | Vecerina et al. |
| 2005/0277096 A1 | 12/2005 | Hendrickson et al. |
| 2006/0073454 A1 | 4/2006 | Hyltander et al. |
| 2007/0035511 A1 | 2/2007 | Banerjee et al. |
| 2007/0172803 A1 | 7/2007 | Hannaford et al. |
| 2007/0207448 A1 | 9/2007 | Glaser et al. |
| 2007/0275359 A1 | 11/2007 | Rotnes et al. |
| 2009/0253109 A1 | 10/2009 | Anvari et al. |
| 2010/0019890 A1 | 1/2010 | Helmer et al. |
| 2010/0291520 A1 | 11/2010 | Kurenov et al. |
| 2015/0005768 A1 | 1/2015 | Sutherland et al. |
| 2017/0340397 A1 | 11/2017 | Smaby et al. |

FOREIGN PATENT DOCUMENTS

| | | |
|---|---|---|
| WO | 2007121572 A1 | 11/2007 |
| WO | 2008033541 A2 | 3/2008 |
| WO | 2008058039 A1 | 5/2008 |

OTHER PUBLICATIONS

Brooks et al., "Project Gropehaptic Displays for Scientific Visualization," ACM SIGGRAPH Computer Graphics, Aug. 1990, vol. 24(2), pp. 177-185.
Burdea., "Haptic Feedback for Virtual Reality," Proceedings of International Workshop on Virtual prototyping, May 1999, pp. 87-96.
Grange et al., "The Delta Haptic Device as a Nanomanipulator," Proceedings of SPIE—The International Society for Optical Engineering, Micro robotics and Micro assembly III 2001, vol. 4568, pp. 100-111.
Howe and Kontarinis., "Task Performance With a Dexterous Teleoperated Hand System," Proceedings of the SPIE, 1992, vol. 1833, pp. 199-207.
International Patent Application No. PCT/CA2018/000243, International Preliminary Report on Patentability dated Apr. 5, 2019.
International Patent Application No. PCT/CA2018/000243, International Search Report and Written Opinion dated Apr. 1, 2019.
Iwata., "Pen-based Haptic Virtual Environment," Proceedings of IEEE Virtual Reality Annual International Symposium, 1993, pp. 287-292.
Maddahi et al., "Quantifying Workspace and Forces of Surgical Dissection During Robot-assisted Neurosurgery," The International Journal of Medical Robotics + Computer Assisted Surgery, 2015, vol. 12(3), pp. 528-537.
Marcus et al., "Exos Research on Master Controllers for Robotic Devices," Fifth Annual Workshop on Space Operations Applications and Research, Jul. 1991, pp. 238-245.
Martin and Trivino.,"A study of the Manipulability of the PHANToM OMNI Haptic Interface," Proceedings of the Third Workshop on Virtual Reality Interactions and Physical Simulations, Jan. 2006.
Massie and Salisbury., "The PHANToM Haptic Interface: A Device for Probing Virtual Objects," DSC-vol. 55-1, Dynamic Systems and Control, 1994, vol. 1.
Snow et al., "Compact Force-Reflecting Hand Controller," NASA Tech Briefs, Apr. 1991, vol. 15(4), 0145-319X.
Sutherland et al., "Merging Machines With Microsurgery: Clinical Experience With Neuroarm," Journal of Neurosurgery, 2013, vol. 118(3), pp. 521-529.
Sutter et al., "Response to Reflected-force Feedback to Fingers in Teleoperations," Proceedings of the NASA Conference on Space Telerobotics, Jan. 1989, vol. 4, pp. 65-74.
Zareinia et al., "Performance Evaluation of Haptic Hand-controllers in a Robot-assisted Surgical System," The International Journal of

(56) References Cited

OTHER PUBLICATIONS

Medical Robotics + Computer Assisted Surgery, 2015, vol. 11(4): pp. 486-501.

* cited by examiner

MICROSURGERY-SPECIFIC HAPTIC HAND CONTROLLER

CROSS-REFERENCE

This application claims the benefit of U.S. Provisional Patent Application Ser. No. 62/611,024 filed Dec. 28, 2017, which is hereby incorporated by reference.

BACKGROUND

Haptic hand-controllers are typically used to command a virtual moving object or a slave manipulator, either industrial or medical. A haptic hand-controller is itself often referred to as a master robot, which is connected to a control station and maneuvered by an operator. In a medical-grade hand controller, besides having a high definition positional feedback, reproducing the force of tool-tissue interaction is important for a surgeon to avoid applying excessive force and damaging the tissue.

A variety of different general-purpose serial, parallel and hybrid haptic devices have been designed, developed and commercialized as master commanders for their corresponding slave manipulators. These tele-operating manipulation systems have different specifications depending on their serial or parallel configuration. They are generally used for virtual reality simulation, game joysticks, entertainment, training, etc. with different degrees of freedom (DOF) associated with positional sensing and force feedback. The history of haptic devices goes back to the 1950s when the first master-slave manipulator was developed In Argonne National Lab, capable of communicating commutatively between a master arm and a slave manipulator, As time progressed, electrical, pneumatic, hydraulic and other sources of driving power were employed in robotic systems.

Tactile feedback was pioneered at Massachusetts Institute of Technology where a dexterous hand master exoskeleton as a tactile joystick was developed using voice coil actuators, Subsequently, the first generation of desktop haptic systems with force feedback was created at the Rutgers University CAIP Centre. That device, demonstrated in 1992, consisted of a few pneumatic actuators to sense the hardness of the objects that were being manipulated virtually. It was followed by presentation of the PHANTOM haptic interface in 1994, which enabled users to feel a wide variety of physical objects in cyberspace and control a remote manipulator.

Since that time, several general-purpose haptic hand-controllers have been introduced; some of them could contribute to medical research labs and robot-assisted surgical systems. Haptic devices employed in medical applications have the aim of making the operations easier and more accurate, besides minimizing the Invasion, complications and pain while shortening the operation time. Currently, the most commonly used haptic interfaces include: da Vinci (Intuitive Surgical Inc., USA); Delta6 and Sigma7 (Force Dimension, Switzerland); Geomagic® Touch™ (formerly Sensable Omni); Geomagic® Touch™ X (formerly Sensable Phantom Desktop), and Geomagic® PHANToM Premium™ families (Geomagic, USA); $HD^2$ (Quanser; Markham, Canada); W3D and W6D haptic devices (Entact, Guelph, Canada); Novint Falcon (Novint Technologies Inc., Albuquerque, USA); and Freedom 7 (MPB Technologies Inc., Canada).

Improvements in haptic hand controllers, particularly those intended for fine manipulation such as microsurgery, are desirable.

BRIEF DESCRIPTION

Figure 1:
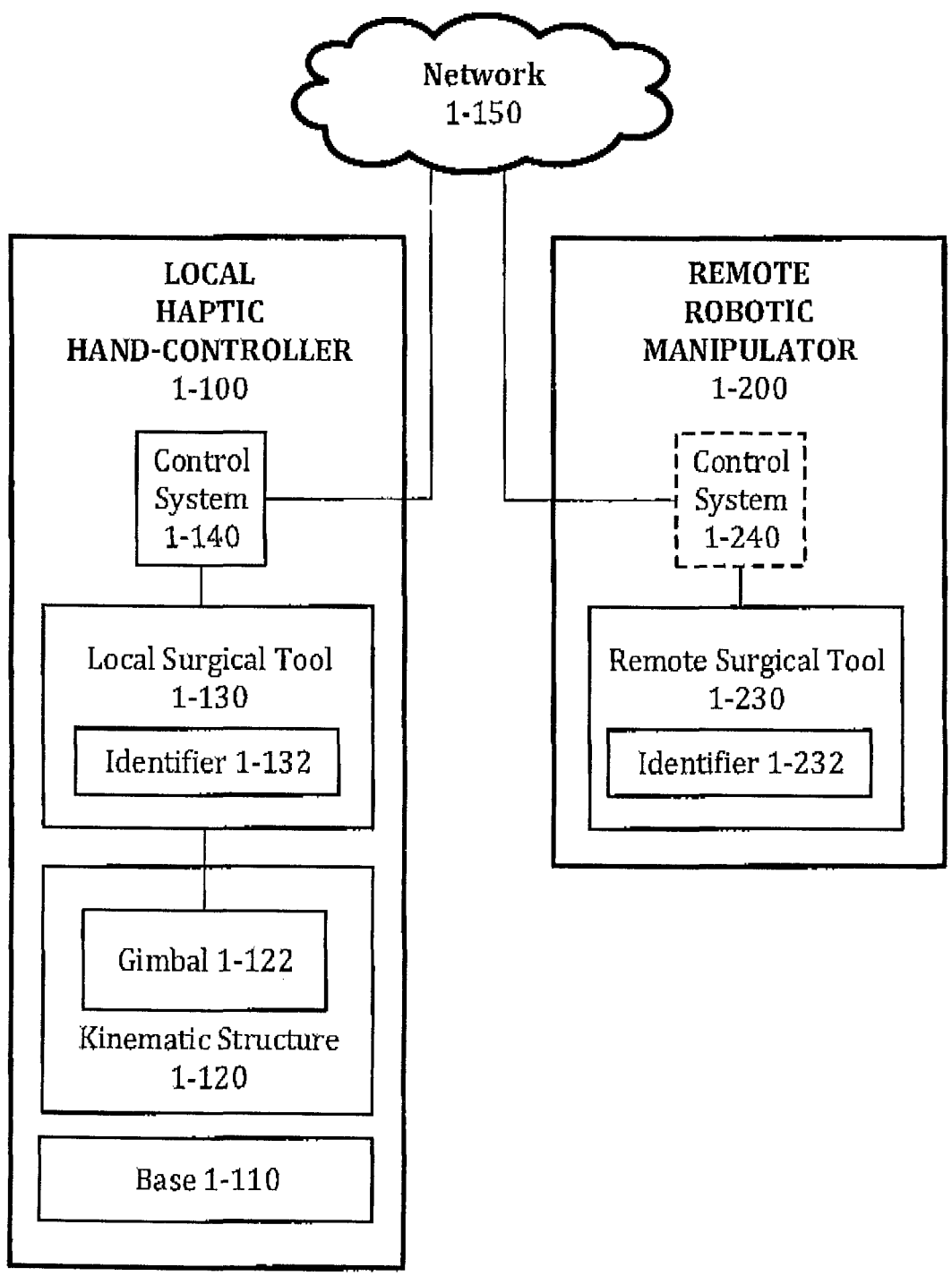
FIG. 1 is a block diagram illustrating a local haptic hand controller according to an embodiment of the present disclosure for enabling an operator to remotely perform microsurgery by controlling a remote robotic manipulator.

In an embodiment, the present disclosure provides a local haptic hand controller for enabling an operator to remotely perform microsurgery by controlling a remote robotic manipulator, the local haptic hand controller comprising: a base; a kinematic structure in communication with the base, the kinematic structure comprising a gimbal provided as an end-effector; a local surgical tool provided at the gimbal and having a shape and construction substantially similar to a remote surgical tool provided at the remote robotic manipulator and with which the microsurgery is to be performed, the local surgical tool comprising a local surgical tool identifier; and a control system in communication with the local surgical tool of and with the remote surgical tool, the control system configured to enable operation of the local haptic hand controller when a local surgical tool identifier matches a remote surgical tool identifier.

In an example embodiment, the local surgical tool comprises a local surgical tool type identifier identifying a type of surgical tool, and wherein the control system is configured to enable operation of the local haptic hand controller when the local surgical tool type identifier matches a remote surgical tool type identifier.

In an example embodiment, the local surgical tool comprises a local individual surgical tool identifier identifying a specific surgical tool, and wherein the control system is configured to enable operation of the local haptic hand controller when the local individual surgical tool identifier matches a remote individual surgical tool identifier.

In an example embodiment, the control system is configured to generate a warning when the local surgical tool identifier does not match the remote surgical tool identifier.

In an example embodiment, the control system is configured to compare the local surgical tool identifier with a remote surgical tool identifier, and to permit operation of the local haptic hand controller only when the local surgical tool identifier matches the remote surgical tool identifier.

In an example embodiment, the control system is provided in communication with, but separate from, the local haptic hand controller.

In an example embodiment, the control system comprises a local control system configured to communicate with the remote surgical tool via a remote control system associated with the remote robotic manipulator.

In an example embodiment, the local haptic hand controller further comprises a human-machine interface configured to provide an output of the control system based on a comparison of the local surgical tool identifier with the remote surgical tool identifier.

In an example embodiment, the local haptic hand controller is configured to perform self-diagnosis and to provide a result of the self-diagnosis.

In an example embodiment, the local haptic hand controller is configured to perform a diagnosis of the local haptic hand controller and to provide a result of the diagnosis.

In an example embodiment, the control system is configured to, based on the remote surgical tool identifier, provide information to the local hand controller to compensate for the weight of the remote surgical tool to reduce inertia or provide haptic force feedback.

In an example embodiment, the local surgical tool comprises at least one sensor, and wherein the local haptic hand controller comprises a self-diagnosis module configured to detect an operational status of the at least one sensor in the local surgical tool.

In an example embodiment, the local surgical tool comprises at least one sensor in communication with the control system.

In an example embodiment, the at least one sensor is selected from the group consisting of: a magnetic sensor, a Hall-effect sensor, an optical sensor, a strain-gauge resistive sensor, a piezo-electric sensor, a piezo-resistive sensor, a capacitive proximity sensor, and an induction sensor.

In an example embodiment, the at least one sensor is configured to measure a distance between first and second prongs of forceps.

In an example embodiment, the at least one sensor is configured to determine a force applied to the forceps by the operator based on the measured distance.

In an example embodiment, the local surgical tool comprises at least one actuator in communication with the control system.

In an example embodiment, the at least one actuator is selected from the group consisting of: electric, electromagnetic, piezoelectric, pneumatic and hydraulic actuator.

In an example embodiment, the at least one actuator is configured to provide high-definition force feedback to enable the operator to feel, at the local surgical tool, force applied to the remote surgical tool.

In an example embodiment, the at least one actuator is configured to generate at least 1-DOF pinching or coagulating haptic force feedback between forceps prongs according to a real-time force applied to a tissue by the remote surgical tool.

In an example embodiment, the local surgical tool comprises a sensorized surgical tool, an actuated surgical tool or a powered surgical tool.

In an example embodiment, the local surgical tool is selected from the group consisting of forceps, bipolar forceps, a suction tube, a dissector, micro scissors, micro dissectors, a power drill, endoscopy tools, tweezers, and a laser.

In an example embodiment, the local surgical tool comprises a dual prong surgical tool having first and second prongs, the dual prong surgical tool comprising at least one position sensor configured to provide positional feedback with respect to a distance between the first and second prongs.

In an example embodiment, the at least one position sensor comprises a Hall-effect sensor provided on either the first or second prong, and further comprising a magnet bar provided on the opposite prong from the Hall-effect sensor, the Hall-effect sensor and the magnet bar cooperating to measure the distance between the first and second prongs.

In an example embodiment, the local surgical tool and the remote surgical tool each comprises a dual prong surgical tool having first and second prongs, the dual prong local surgical tool comprising at least one actuation mechanism configured to generate haptic force feedback at a local site based on a force sensed between first and second prongs of the remote dual prong surgical tool.

In art example embodiment, the local surgical tool comprises a measuring device configured to measure a roll angle.

In an example embodiment, the local surgical tool comprises, on at least one end point of the local surgical tool, a push-pull locking connector to facilitate installation and removal of the local surgical tool with respect to the gimbal.

In an example embodiment: the local surgical tool comprises at least one sensor configured to measure operator parameters including position, orientation and forces applied by the operator, and the control system is configured to compare the measured operator parameters to stored reference parameters to assess operator performance.

In an example embodiment, the local surgical tool comprises a suction device including sensing actuator, the sensing actuator configured to: sense an amount of pressure applied by the operator to the sensing actuator; and control a flow rate of the suction device based on the sensed amount of pressure.

In an example embodiment, the local surgical tool comprises an encoding connector in communication with the control system and configured to encode the local surgical tool with the local surgical tool identifier.

In an example embodiment, the encoding connector is configured to encode the local surgical tool with a local surgical tool type identifier.

In an example embodiment, the encoding connector is configured to encode the local surgical tool with a local individual surgical tool identifier.

In an example embodiment, the encoding connector is configured to obtain or measure local surgical tool status data and to provide the local surgical tool status data to the control system.

In an example embodiment, the gimbal comprises an end-effector having at least 3 degrees-of-freedom and having three independent rotational joints configured to mimic wrist motion.

In an example embodiment, the gimbal comprises a single-prong tool connector including a prong holder configured for mating with a single-prong local surgical tool.

In an example embodiment, the single-prong tool connector is selected from the group consisting of: a push-pull locking connector, a bayonet connector, and a threaded lock-type connector.

In an example embodiment, the gimbal comprises a dual-prong tool connector defining at least one prong holder configured for mating with at least one prong of a dual-prong local surgical tool.

In an example embodiment, the at least one prong holder comprises at least one miniaturized clamp configured to fix the at least one prong of the dual-prong surgical tool at a tool lower end.

In an example embodiment, the gimbal comprises a dual-prong tool connector defining first and second prong holders configured for mating with first and second prongs of a dual-prong local surgical tool.

In an example embodiment, the gimbal comprises at least one positional feedback sensor configured to measure roll, pitch or yaw.

In an example embodiment, the at least one positional feedback sensor comprises three positional feedback sensors configured to measure roll, pitch and yaw.

In an example embodiment, the at least one positional feedback sensor comprises one or more rotary encoders, one or more potentiometers, or one or more resolvers, or a combination thereof.

In an example embodiment, the gimbal comprises a gimbal frame and a tool connector, the tool connector provided below the gimbal frame and configured to connect with the local surgical tool at a tool top end such that, in operation, the tool and the operator's hand are positioned underneath the gimbal frame.

In an example embodiment, the gimbal comprises a gimbal frame and a tool connector, the tool connector provided above the gimbal frame and configured to connect with the local surgical tool at a tool lower end such that, in operation, the tool and the operator's hand are positioned above the gimbal frame.

In an example embodiment, the gimbal comprises gimbal joints and wherein the gimbal provides at least 4 degrees-of-freedom positional feedback, and at least three degrees-of-freedom on the gimbal joints.

In an example embodiment, the gimbal is configured to provide at least three rotational degrees of freedom Including roll, pitch and yaw, to replicate finger, hand and wrist motions.

In an example embodiment, the gimbal comprises at least two gimbal links, at least three gimbal joints and at least three measuring means configured to provide at least pronation/supination and flexion/extension degrees of freedom to the operator's hand/finger relative to the operator's forearm.

In an example embodiment, the kinematic structure comprises a plurality of serial linkages, and wherein the plurality of serial linkages and the gimbal cooperate, in use, to mimic human upper limb and hand motion.

In an example embodiment, the kinematic structure comprises a plurality of serial linkages shaped and constructed similar to a human upper extremity.

In an example embodiment, the local haptic hand controller comprises at least nine positional degrees of freedom, and at least four force degrees of freedom.

In an example embodiment, the kinematic structure comprises an articulated structure including a plurality of serial linkages, the articulated structure having at least three positional degrees of freedom, and at least four force degrees of freedom.

In an example embodiment, the kinematic structure comprises at least one linkage arm having at least three translational degrees of freedom to replicate human elbow and shoulder motion.

In an example embodiment, the kinematic structure comprises at least one linkage arm comprising at least three actuators installed on the linkage arm to provide at least 3 degrees of force feedback.

In an example embodiment, the kinematic structure comprises a plurality of serial linkages, the plurality of serial linkages and the gimbal cooperating, in use, to translate operator arm movement into movement of at least one of the plurality of linkages in a direction parallel to and side-by-side with the operator arm movement.

In an example embodiment, the operator arm movement is caused by a first serial link chain defined by the operators arm, and the plurality of linkages comprise a second serial link chain configured to move in parallel with, and together with, the first serial link chain.

In an example embodiment, the kinematic structure comprises a shoulder, which facilitates a flexion/extension degree of freedom for the operator for physically exchanging at least one component of a 3-dimensional force vector with an operators hand/finger.

In an example embodiment, the kinematic structure comprises two links and two joints which facilitate both the abduction/adduction and internal/external rotational degrees of freedom for physically exchanging at least two components of a 3-dimensional force vector with an operator's hand/finger.

In an example embodiment, the two links comprise an upper arm and a forearm, and wherein the two joints comprise an upper elbow joint provided at a first end of the upper arm, and a lower elbow joint provided between a second end of the upper arm and the forearm.

In an example embodiment, the kinematic structure comprises: a shoulder assembly; an upper arm pivotally connected to the shoulder assembly; a lower elbow joint pivotally connected to a lower end of the upper arm; and a forearm pivotally connected to the lower elbow joint, and the gimbal is pivotally connected to the forearm.

In an example embodiment, the shoulder assembly comprises: a rotary joint; and an upper elbow joint coupled to the rotary joint.

In an example embodiment, the local haptic hand controller further comprises a power transmission device in communication with the upper and lower elbow joints, wherein the power transmission device is configured to transmit power from an actuator of the upper elbow joint to an axis of the lower elbow joint.

In an example embodiment, the kinematic structure is adapted to exert forces and/or torques for at least partial compensation of gravity related forces.

In an example embodiment, the kinematic structure is adapted to exert torques acting in at least one of three translational degrees of freedom.

In an example embodiment, the kinematic structure comprises a shoulder, an upper arm and a forearm, and further comprising actuators configured to power three independent freedoms of the upper arm and the forearm relative to the shoulder to provide the at least partial gravity compensation.

In an example embodiment, the local haptic hand controller and the local surgical tool comprise a master hand controller and a master surgical tool, and wherein the remote robotic manipulator and the remote surgical tool comprise a slave haptic hand controller and a slave surgical tool.

In an example embodiment, the local haptic hand controller further comprises a static counterbalance assembly comprising: a pendulum fixed to a shaft; and a counterweight secured to the pendulum such that the counterweight swings around the axis to which the pendulum is fixed.

In an example embodiment, the local haptic hand controller further comprises a motorized dynamic counterbalance assembly comprising: a dynamic counterweight; a gear motor in communication with the control system and coupled to the dynamic counterweight, the gear motor configured to Move the counterweight in response to a dynamic counterbalance signal received from the control system.

In an example embodiment, the local haptic hand controller further comprises the motorized dynamic counterbalance assembly comprises: a vertical motion compartment configured to move the counterweight up and down manually; and a horizontal motion compartment configured to move the counterweight right and left automatically.

In another embodiment, the present disclosure provides a local haptic hand controller for enabling an operator to remotely perform microsurgery by controlling a remote robotic manipulator, the local haptic hand controller comprising: a base; a kinematic structure in communication with the base, the kinematic structure comprising a plurality of serial linkages and comprising a gimbal provided as an end-effector, the plurality of serial linkages and the gimbal cooperating, in use, to translate operator arm movement into movement of at least one of the plurality of linkages in a direction parallel to and side-by-side with the operator arm movement; and a control system in communication with the remote surgical tool and with a local surgical tool adapted for mating with the gimbal, the control system configured to enable operation of the local haptic hand controller when a local surgical tool identifier associated with the local surgical tool matches a remote surgical tool identifier associated with the remote surgical tool.

In an example embodiment, the operator arm movement is caused by a first serial link chain defined by the operator's arm, and the plurality of linkages comprise a second serial link chain configured to move in parallel with, and together with, the first serial link chain.

In an example embodiment, the kinematic structure comprises: a shoulder assembly including a rotary joint and an upper elbow joint coupled to the rotary joint; an upper arm pivotally connected to the shoulder assembly; a lower elbow joint pivotally connected to a lower end of the upper arm; and a forearm pivotally connected to the lower elbow joint, and wherein the gimbal is pivotally connected to the forearm.

In a further embodiment, the present disclosure provides a local haptic hand controller for enabling an operator to remotely perform microsurgery by controlling a remote robotic manipulator, the local hectic hand controller comprising: a base: a kinematic structure in communication; with the base, the kinematic structure comprising a plurality of serial linkages and comprising a gimbal provided as an end-effector, the plurality of serial linkages and the gimbal cooperating, in use, to translate operator arm movement into movement of at least one of the plurality of linkages in a direction parallel to and side-by-side with the operator arm movement, the plurality of serial linkages comprising: a shoulder assembly including a rotary joint and an upper elbow joint coupled to the rotary joint; an upper arm pivotally connected to the shoulder assembly; a lower elbow joint pivotally connected to a lower end of the upper arm; and a forearm pivotally connected to the lower elbow joint; the gimbal being pivotally connected to the forearm; and a local surgical tool provided at the gimbal and having a shape and construction substantially similar to a remote surgical tool provided at the remote robotic manipulator and with which the microsurgery is to be performed, the local surgical tool configured to communicate over the network with the remote robotic manipulator to control operation of the remote surgical tool based on operator movement of the local surgical tool.

In an embodiment, the present disclosure provides a local haptic hand controller for enabling an operator to remotely perform fine manipulation by controlling a remote robotic manipulator, the local haptic hand controller comprising: a base; a kinematic structure in communication with the base, the kinematic structure comprising a gimbal provided as an end-effector; a local fine manipulation tool provided at the gimbal and having a shape and construction substantially similar to a remote fine manipulation tool provided at the remote robotic manipulator, the local fine manipulation tool comprising a local fine manipulation tool identifier; and a control system in communication with the local fine manipulation tool and with the remote fine manipulation tool, the control system configured to enable operation of the local haptic hand controller when a local fine manipulation tool identifier matches a remote fine manipulation tool identifier.

DETAILED DESCRIPTION

A local haptic hand controller is provided for enabling an operator to remotely perform fine manipulation, such as microsurgery, in conjunction with a remotely located robotic manipulator, for example at which the microsurgery is to be performed. The local haptic hand controller includes a base, a kinematic structure in communication with the base and comprises a gimbal as an end effector. A local surgical tool is provided at the gimbal and has a shape and construction substantially similar to a remote surgical tool provided at the remote robotic manipulator. A control system is in communication with the local surgical tool and with the remote surgical tool, and configured to enable operation of the local haptic hand controller when a local surgical tool identifier matches a remote surgical tool identifier.

Microsurgery refers to a type of surgery in which a surgeon or operator uses a visual output of a microscope in order to perform the surgery. The visual output of the microscope is typically proved on a screen suitable for viewing while performing the surgery. In the context of remote surgery, at the remote site in an example implementation, a microscope op rates at the surgery side and the view of the microscope is transmitted to the local site at which the operator manipulates a local hand controller. As soon as a microscope is being used for surgery, such as in microsurgery, the tools used for the surgery are different. The tools typically used for microsurgery are bipolar forceps, suction, dissector, and micro scissors, with bipolar forceps and suction not being limited for use in microsurgery.

A microsurgery-specific haptic hand-controller is provided for intuitive and commutative haptic interaction with an operator, for example in a tele-operated environment. In an implementation, the haptic device comprises an articulated structure and at least nine positional degrees of freedom, and at least four force degrees of freedom. In an implementation, the device is designed such that a wide range of force is secured with high position accuracy and repeatability. For an intuitive translational manipulability, the system includes a linkage design similar to the human upper extremity. Ease of motion is provided by a workspace comparable to that of conventional surgery, considering optimal structural link lengths and global conditioning index. This is further improved by the inclusion of a gimbal as a specific exchangeable end-effector. In example implementations, the gimbal is configured to enhance rotational manipulability and engagement with task-specific tool attachments to provide a similar mechanism for actuation as in conventional surgery. In an embodiment, high definition force feedback is provided at the tool level to improve the safety and performance of robot-assisted surgery, for example by avoidance of force errors in execution of delicate surgical tasks.

Embodiments of the present disclosure are also provided for other types of fine manipulation outside of microsurgery, such as fine manipulation of objects in a laboratory. For instance, a local haptic hand controller according to an embodiment of the present disclosure can be used to perform fine manipulation of laboratory objects at a remote location, for example in a quarantined area. In such an implementation, a remote fine manipulation tool is controlled by the local haptic hand controller.

In an implementation, the local haptic hand controller is configured to provide minimal friction and inertia by means of one or more of: lightweight components, revolute joints, low-friction bearings, and precise dimensional and geometrical tolerances. In an implementation, an adjustable base is provided to further improve ergonomics. In another implementation, mounting three actuators symmetrically on the shoulder frame improves gravity compensation; implementing a static counterbalance, and optionally implementing a motorized dynamic counterbalance, further improves gravity compensation. Embodiments of the present disclosure accommodate encoded exchangeable surgical or industrial tools, ideal for implementation in robot-assisted microsurgery and other gaming/industrial haptic applications.

An ideal microsurgery-specific haptic hand-controller preferably has one or more of the following characteristics: be Intuitive, dexterous, stiff, sensitive and possesses accurate motion mapping, high position and force feedback resolutions, motion smoothness, small gimbal size, the minimum possible weight and mass inertia, high manipulability, isotropy, and optimum kinematic performance.

FIG. 1 is a block diagram illustrating a local haptic hand controller according to an embodiment of the present disclosure for enabling an operator to remotely perform microsurgery by controlling a remote robotic manipulator. In an embodiment, the local haptic hand controller 1-100 enables an operator to remotely perform microsurgery in conjunction with a remote robotic manipulator 1-200 at which the microsurgery is performed. In an implementation, the local haptic hand controller 1-100 is in communication with the remote robotic manipulator 1-200 over a network 1-150. The local haptic hand controller 1-100 comprises: a base 1-110; a kinematic structure 1-120 in communication with the base 1-110, the kinematic structure 1-120 comprising a gimbal 1-122 provided as an end-effector; and a local surgical tool 1-130. The local surgical tool 1-130 is provided at the gimbal 1-122 and has a shape and construction substantially similar to a remote surgical tool 1-230 provided at the remote robotic manipulator 1-200 at which the microsurgery is to be performed. In an embodiment, the remote surgical tool 1-230 is the actual tool used in the procedure, and the local surgical tool 1-130 has substantially the same shape and construction, in contrast to arrangements in which an operator at a local or master robot manipulates a joystick or other controller that is very dissimilar to the actual surgical tool. In an embodiment, the local surgical tool comprises a local surgical tool identifier 1-132.

In an embodiment, the local haptic hand controller 1-100 further comprises a control system 1-140 in communication with the local surgical tool 1-130 and with the remote surgical tool 1-230. In an embodiment, the control system 1-140 is configured to enable operation of the local haptic hand controller when a local surgical tool identifier matches a remote surgical tool identifier. In an example embodiment, the local surgical tool comprises a local surgical tool type identifier identifying a type of surgical tool, or family of surgical tool; in such an implementation, the control system is configured to enable operation of the local haptic hand controller when the local surgical tool type identifier matches a remote surgical tool type identifier. In an example embodiment, the local surgical tool comprises a local individual surgical tool identifier identifying a specific surgical tool, as opposed to a family of surgical tools or a type of surgical tool; in such an implementation, the control system is configured to enable operation of the local haptic hand controller when the local individual surgical tool identifier matches a remote individual surgical tool identifier.

In an embodiment, the control system 1-140 generates a warning when the local and remote surgical tool identifiers do not match. In another embodiment, the control system 1-140 is configured to compare the local surgical tool identifier with a remote surgical tool identifier, and to permit operation of the local haptic hand controller only when the local surgical tool identifier matches the remote surgical tool identifier. In an alternative embodiment, the control system 1-140 is provided in communication with, but separate from, the local haptic hand controller 1-100. In an example embodiment, the control system comprises a local control system 1-140 configured to communicate with the remote surgical tool via a remote control system 1-240 associated with the remote robotic manipulator 1-200.

The remote robotic manipulator 1-200 comprises a remote surgical tool 1-230 including a remote surgical tool identifier 1-232. The remote robotic manipulator 1-200 optionally includes a base, such as an adjustable base. In an embodiment, the base 1-110 in the local haptic hand controller 1-100 comprises an adjustable base that provides customization so that an operator is as comfortable as possible; such customization may not be needed at the remote robotic manipulator.

Embodiments of the present disclosure provide a local (master) haptic device specifically designed for robotic tele-operated microsurgery in a non-local environment to be paired with a remote (slave) manipulator to perform a surgical task for surgeons of different training levels and experience. In an example embodiment, the local haptic hand controller and the local surgical tool comprise a master hand controller and a master surgical tool, and wherein the remote robotic manipulator and the remote surgical tool comprise a slave haptic hand controller and a slave surgical tool.

Embodiments of the present disclosure provide a haptic device that realizes the aspirations of the end operator to address the challenges related to robot-assisted surgery. In spite of the application of several commercial general-purpose haptic devices in surgery, known approaches have some limitations and are not designed to address all the demands of microsurgery. Embodiments of the present disclosure can benefit both the surgeons and the patients to eventually attain higher level of safety and operating success rate.

Embodiments of the present disclosure are aimed at minimizing one or more of: the training time (for novice operators), effort time to do a task, weight, and mass inertia. This is achieved while moving towards one or more of: a higher level of ergonomics, improved kinematic performance, ease of motion, intuitiveness, manipulability, force resolution, safety, sensitivity, accuracy and precision.

Embodiments of the present disclosure generally provide a haptic hand controller comprising a local side for a tele-operative local-remote or master-slave surgical workstation, which can be used in a number of domains, for example the clinical and educational domains, or tele-operative robotic system, where robotic manipulator is the remote side. Embodiments of the present disclosure are equally applicable to both clinical and educational applications, but are not limited thereto, and are also applicable in industrial, laboratory and gaming applications.

Figure 2:
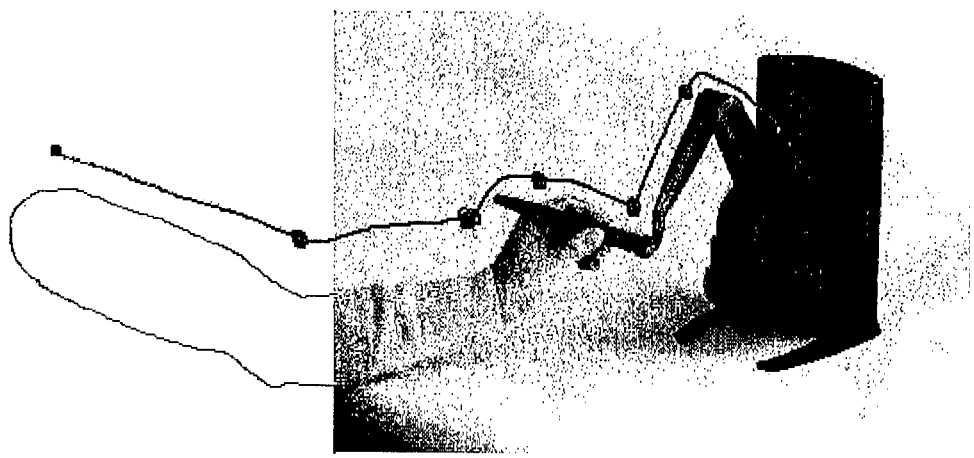
FIG. 2 illustrates a known hand controller in use.

FIG. 2 illustrates a known hand controller in use. In known hand-controllers, the device and the end-effector (gimbal) are placed in front of the user, creating a continuous long serial link chain, which is difficult to maneuver when the size of the device/links increases.

Figure 3:
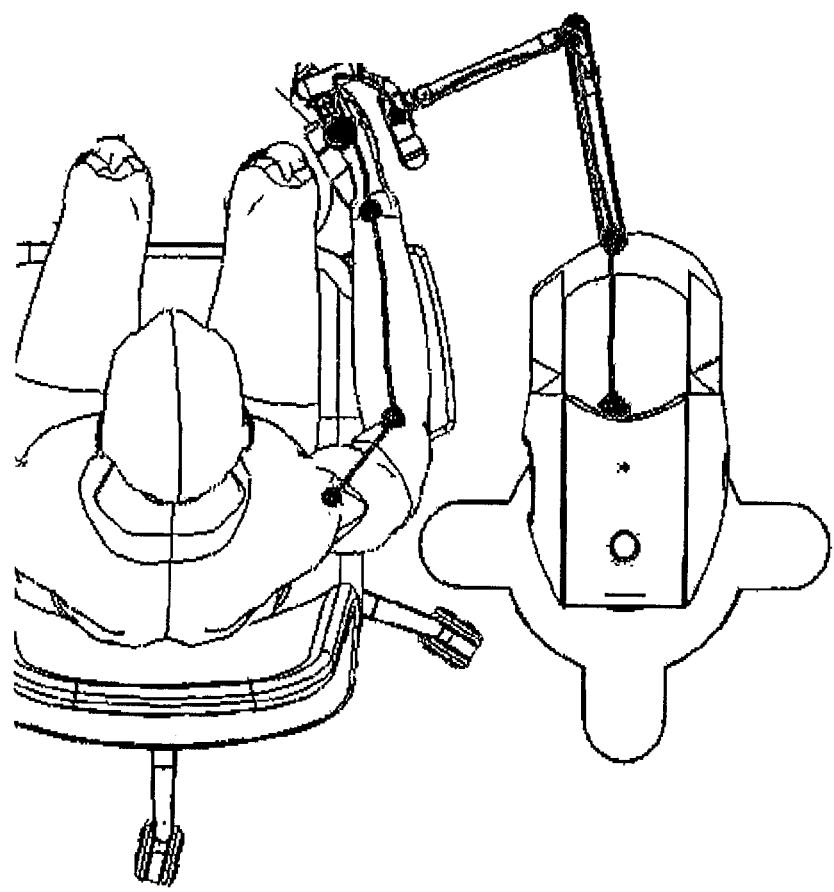
FIG. 3 illustrates a local haptic hand controller according to an embodiment of the present disclosure in use and showing a relationship between operator movement and device movement.

FIG. 3 illustrates a local haptic hand controller according to an embodiment of the present disclosure in use and showing a relationship between operator movement and device movement. According to an embodiment of the present disclosure, the haptic device and end-effector or gimbal are placed side-by-side the user, and users upper limb; this makes two parallel serial link chains moving together, usually in the same direction as the user's hand. This configuration advantageously reduces the training time for operators. The design of the kinematic structure and the gimbal, as further described and illustrated herein, can further improve the ergonomics, ease of motion, and training time.

in an example embodiment, the kinematic structure comprises a plurality of serial linkages, and the plurality of serial linkages and the gimbal cooperate, in use, to mimic human upper limb and hand motion. In another example embodiment, the kinematic structure comprises a plurality of serial linkages shaped and constructed similar to a human upper extremity.

In an example embodiment, the kinematic structure comprises a plurality of serial linkages, the plurality of serial linkages and the gimbal cooperating, in use, to translate operator arm movement into movement of at least one of the plurality of linkages in a direction parallel to and side-by-side with the operator arm movement. In an example embodiment, the operator arm movement is caused by a first serial link chain defined by the operator's arm, and the plurality of linkages comprise a second serial link chain configured to move in parallel with, and together with, the first serial link chain.

In accordance with embodiments of the present disclosure, the local haptic hand controller provides a remarkable intuitive sense, for example providing ease of motion from the aspect of the apparatus in terms of kinematic and dynamic conditions, and/or ease of maneuvering from the aspect of the operator skills and performance. Many experts agree that intuition is related to mental matching. Intuition gets better with practice through recurring events or patterns. The more familiar one is with a certain domain, the faster their brain processes heuristic solutions for a certain situation. A specific region of the brain thought to be Important for intuition is the ventromedial prefrontal cortex, where the information regarding past events is stored. The brain normally conducts a brief search of its existing files and presents the best solution for the condition at hand. Implementation of embodiments of the present disclosure can significantly diminish the human brain's searching and matching time and thus facilitate the training process for novice surgeons and residents. Thereby, an operator of a local haptic hand controller according to an embodiment of the present disclosure can conduct a designated surgical task more quickly, with less effort time, and possibly with a shorter trajectory path of the tool tip.

Figure 4:
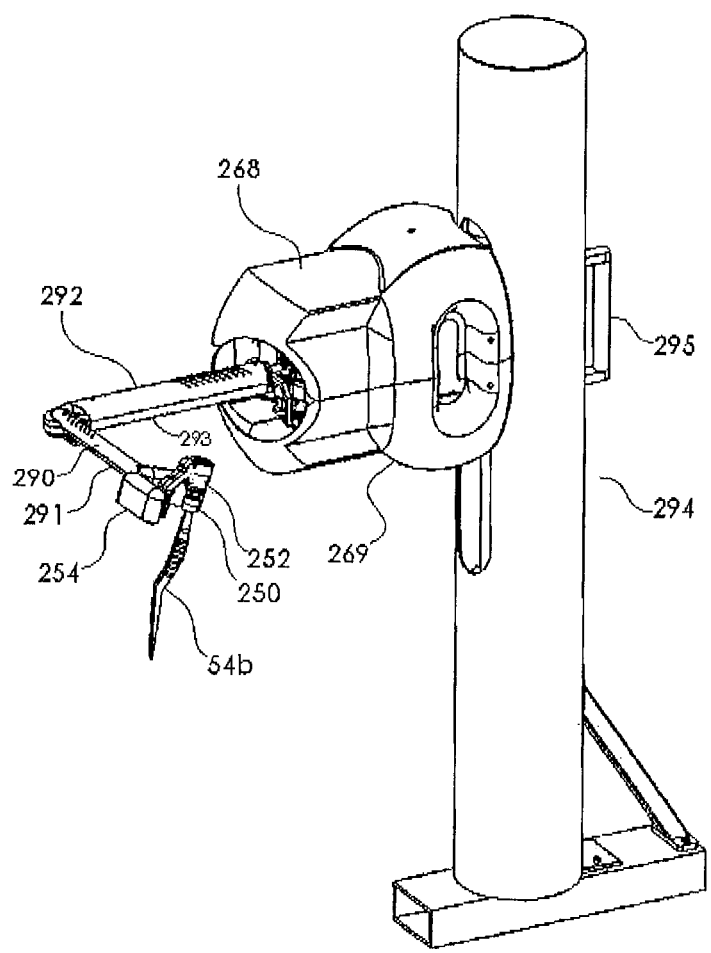
FIG. 4 illustrates a local haptic hand controller according to an embodiment of the present disclosure.

FIG. 4 illustrates a local haptic hand controller according to an embodiment of the present disclosure. In the embodiment of FIG. 4, the base comprises an adjustable base. In an example embodiment, the base is adjustable by movement of a handle bar 295 provided on a base enclosure 294. The local haptic hand controller of FIG. 4. is configured for right-hand use by an operator. The base can be moved by the user through the handle bar 295. In an embodiment, a linear actuator including a linear actuator rod is driven vertically, for example by a DC electromotor that facilitates the height adjustment of the base. The linear actuator can be driven by electrical, pneumatic, hydraulic or other types of driving systems. In an embodiment, a stepper motor and gearbox provide the user with pan rotational motion for further base adjustment.

In an example embodiment, the gimbal comprises a gimbal frame 254 and a tool connector 250, and an encoder 252. In an embodiment, the encoder 252 is configured to encode the local surgical tool identifier. In another embodiment, the encoder 252 is configured to measure one or more displacement angles of the gimbal frame and tool. The tool connector 250 is provided below the gimbal frame 254 and configured to connect with the local surgical tool 54*b* at a tool top end such that, in operation, the tool and the operator's hand are positioned underneath the gimbal frame. As shown in the example embodiment of FIG. 4, one or more portions of the local haptic hand controller can be covered, such as by enclosures 268, 269, detachable lower arm covers 290 and 291, detachable upper arm covers 292 and 293.

Figure 5:
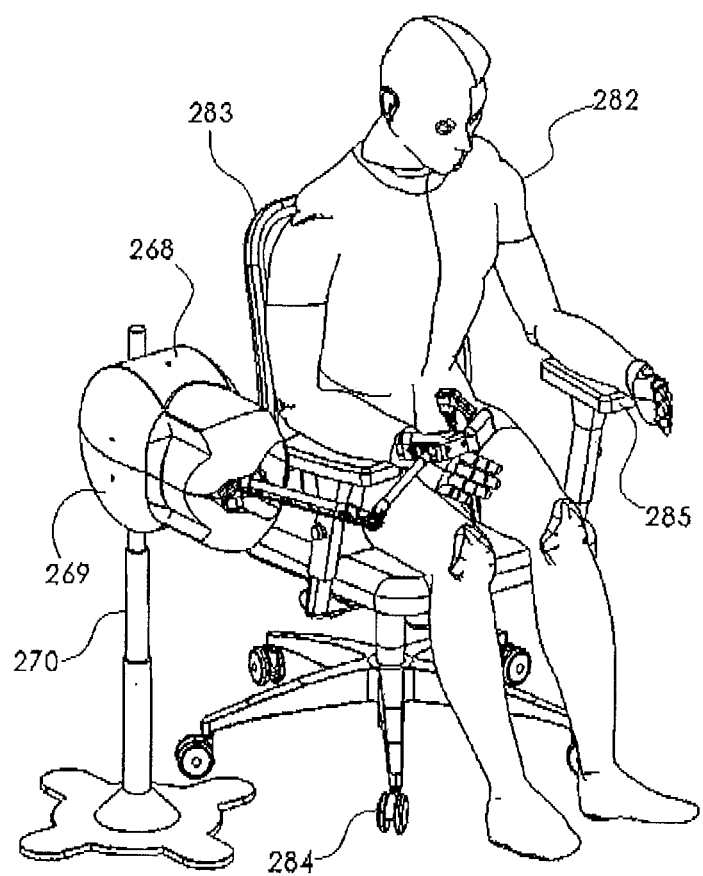
FIG. 5 illustrates a local haptic hand controller according to an embodiment of the present disclosure in right hand use by an operator.

FIG. 5 illustrates a local haptic hand controller similar to FIG. 4, using a different type of adjustable base, according to an embodiment of the present disclosure in right hand use by an operator. The base 270 can be an adjustable base, or a fixed stand placed on the floor, which does not provide the user with any additional ergonomic degrees of freedom for pre-adjustments. In the example embodiment of FIG. 5, the operator/end-user/surgeon 282 sits in a chair 283 provided with wheels 284, with the operator's upper limb rested on arm rests 285 of the chair 283.

In example embodiments such as in FIG. 4 and FIG. 5, the adjustable base can be implemented in different manners. In an example embodiment, the local haptic hand controller comprises at least one human machine interface (HMI) or a computer-based touch panel, which acts as a control station for the base. In an embodiment, the adjustable base is controlled directly by the control system, which can comprise control software, in conjunction with a graphical user interface (see, for example, FIG. 8 and FIG. 11) through a touch screen or manually by force resistive sensors disposed on the base, which allow for the selection of a favorable posture in manual state. In another embodiment, the desired settings can be adjusted manually through a joystick or remote control connected to the control system. Individual users can record preset settings and recall them when needed. This feature allows for defining a home position for the base or recalling the preset home positions.

In an example embodiment, the local haptic hand controller comprises at least one sound module connected to at least one speaker (see element 56 in FIG. 10) to audibly guide the operator through the programmed Interface module, for example to guide the operator through the base setup, step by step; in an embodiment, the audible guides of the sound module are generated based on a signal received from the control system. In an example embodiment, the control system comprises at least two push buttons for moving the entire mechanism up or down, which can be pressed by the operator to adjust the base height. In an alternate embodiment, a fixed base is a simple stand useful for the users who do not need this level of adjustability/ ergonomics.

In an example embodiment, the local haptic hand controller comprises a graphical user interface through which the local surgical tool is checked and monitored. The control system is configured to warn, such as by providing an indication on the GUI, if the local surgical tool on the hand controller is not matched with the corresponding remote surgical tool on the remote robotic manipulator. In an example embodiment, the local haptic hand controller comprises a human-machine interface configured to provide an output of the control system based on a comparison of the local surgical tool identifier with the remote surgical tool identifier.

In an example embodiment, the local haptic hand controller is configured to perform self-diagnosis and to provide a result of the self-diagnosis. In an embodiment, the control system is involved in diagnosis of tools to detect any damage or break down. In an example embodiment, the local haptic hand controller is configured to perform a diagnosis of the local haptic hand controller and to provide a result of the diagnosis. In an example embodiment, the control system of the local haptic hand-controller comprises a self-diagnosis module configured to detect any damaged, broken-down or out-of-order sensors, either in the hand controller or the attached tool, by performing a preliminary checkup of any sensors. In an example embodiment, the local surgical tool comprises at least one sensor, and the local haptic hand controller comprises a self-diagnosis module configured to detect an operational status of the at least one sensor in the local surgical tool.

Recognition of the attached surgical tool provides information for the control software to compensate for the weight of the attached surgical tool. In an example embodiment, the control system is configured to, based on the remote surgical tool identifier, provide information to the local hand controller to compensate for the weight of the remote surgical tool to reduce inertia or provide haptic force feedback.

Figure 6:
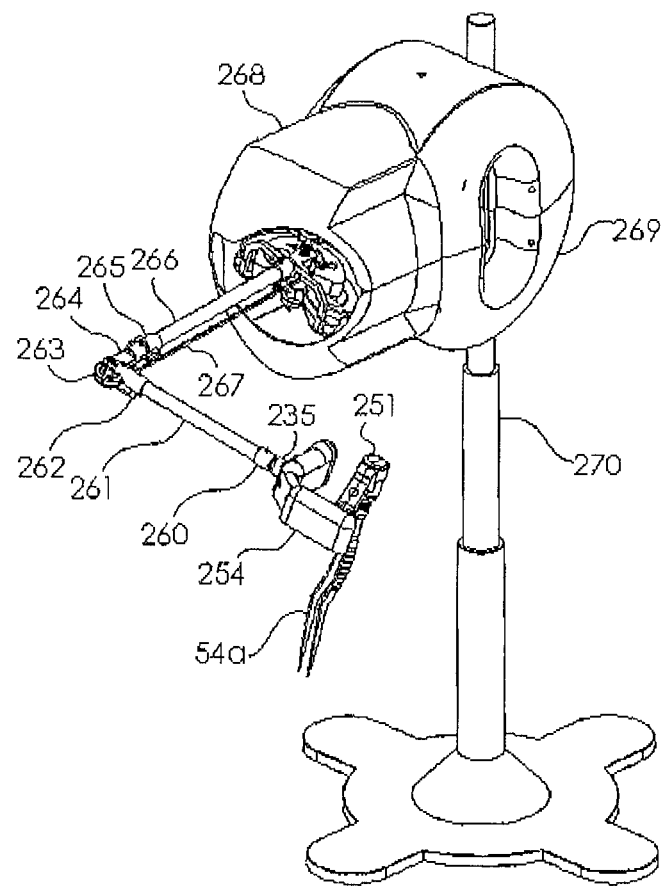
FIG. 6 illustrates a local haptic hand controller according to another embodiment of the present disclosure configured for right hand use by an operator and using a first type of gimbal and a first type of tool.

FIG. 6 illustrates a local haptic hand controller according to an embodiment of the present disclosure configured for right hand use by an operator and using a first type of gimbal and a first type of tool. The type of gimbal used in FIG. 6 is similar to FIG. 4 and FIG. 5, namely with the tool 54a connecting below the gimbal frame 254 at a top end of the local surgical tool 54a such that, in operation, the tool 54a and the operators' hand are positioned underneath the gimbal frame 254. The type of tool Illustrated in FIG. 6 is a dual prong tool, such as forceps. In the example embodiment of FIG. 6, the gimbal comprises a dual-prong tool connector defining at least one prong holder configured for mating with at least one prong of a dual-prong local surgical tool. In an example embodiment, the at least one prong holder comprises at least one miniaturized clamp configured to fix the at least one prong of the dual-prong surgical tool at a tool lower end. In an example embodiment, the gimbal comprises a dual-prong tool connector defining first and second prong holders configured for mating with first and second prongs of the dual-prong local surgical tool.

As shown, in the example embodiment of FIG. 6, one or more portions of the local haptic hand controller can be covered, such as by enclosures 268, 269, pillow tubes or pillow blocks 260, 262, 264, 265 and a flanged tube 235. The local haptic hand controller comprises a forearm link 261, a power transmitter (such as a timing pulley/sprocket) 263, an upper arm link 266 and a transmitter (such as a timing belt or synchronous chain) 267. In an embodiment, an encoder 251 is configured to encode the local surgical tool identifier. In another embodiment, the encoder 251 is configured to measure one or more displacement angles of the gimbal frame and tool.

Figure 7:
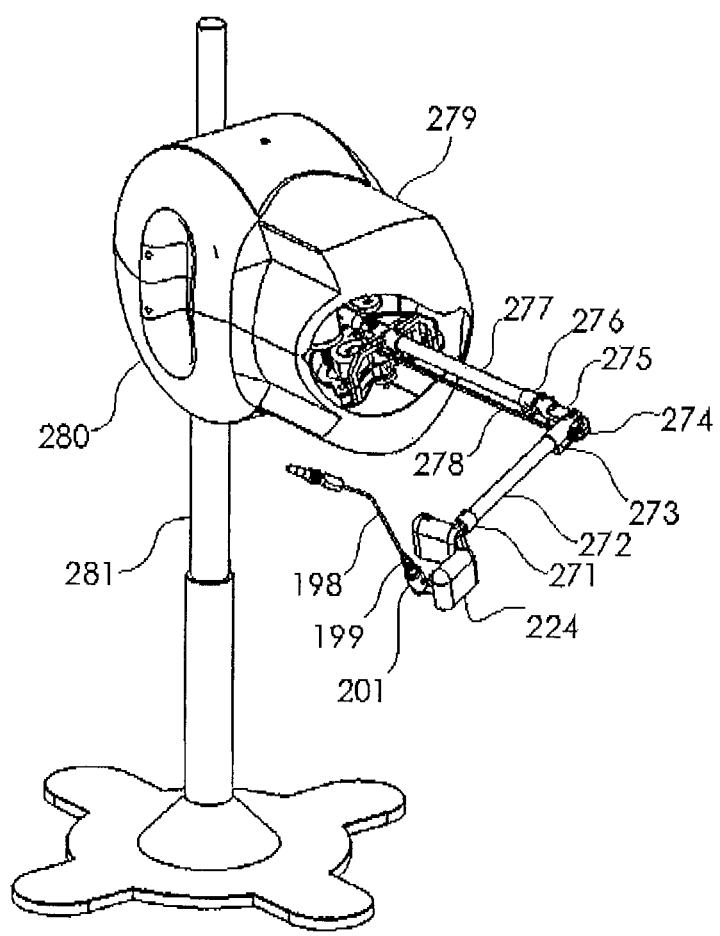
FIG. 7 illustrates a local haptic hand controller according to another embodiment of the present disclosure configured for left hand use by an operator and using a second type of gimbal and a second type of tool.

FIG. 7 illustrates a local haptic hand controller according to another embodiment of the present disclosure configured for left hand use by an operator and using a second type of gimbal and a second type of tool. In the example embodiment of FIG. 7, the gimbal comprises a gimbal frame 224 and a tool connector 201. The tool connector 201 is provided above the gimbal frame 224 and configured to connect with the local surgical tool 198 at a tool lower end such that, in operation, the tool 198 and the operator's hand are positioned above the gimbal frame 224. The type of tool illustrated in FIG. 7 is a single prong tool, such as a suction tool. In the example embodiment of FIG. 7, the gimbal comprises a single-prong tool connector 201 including a prong holder 199 configured for mating with a single-prong local surgical tool. In an example embodiment, the single-prong tool connector is selected from the group consisting of: a push-pull locking connector, a bayonet connector, and a threaded lock-type connector. As shown in the example embodiment of FIG. 7, one or more portions of the local haptic hand controller can be covered, such as by enclosures 279, 280, moveable with respect to the adjustable base 281, pillow tubes or pillow blocks 271, 273, 275, 276. The local haptic hand controller comprises a forearm link 272, a power transmitter (such as a timing pulley/sprocket) 274, an upper arm link 277 and a transmitter (such as a timing belt or synchronous chain) 278.

Figure 8:
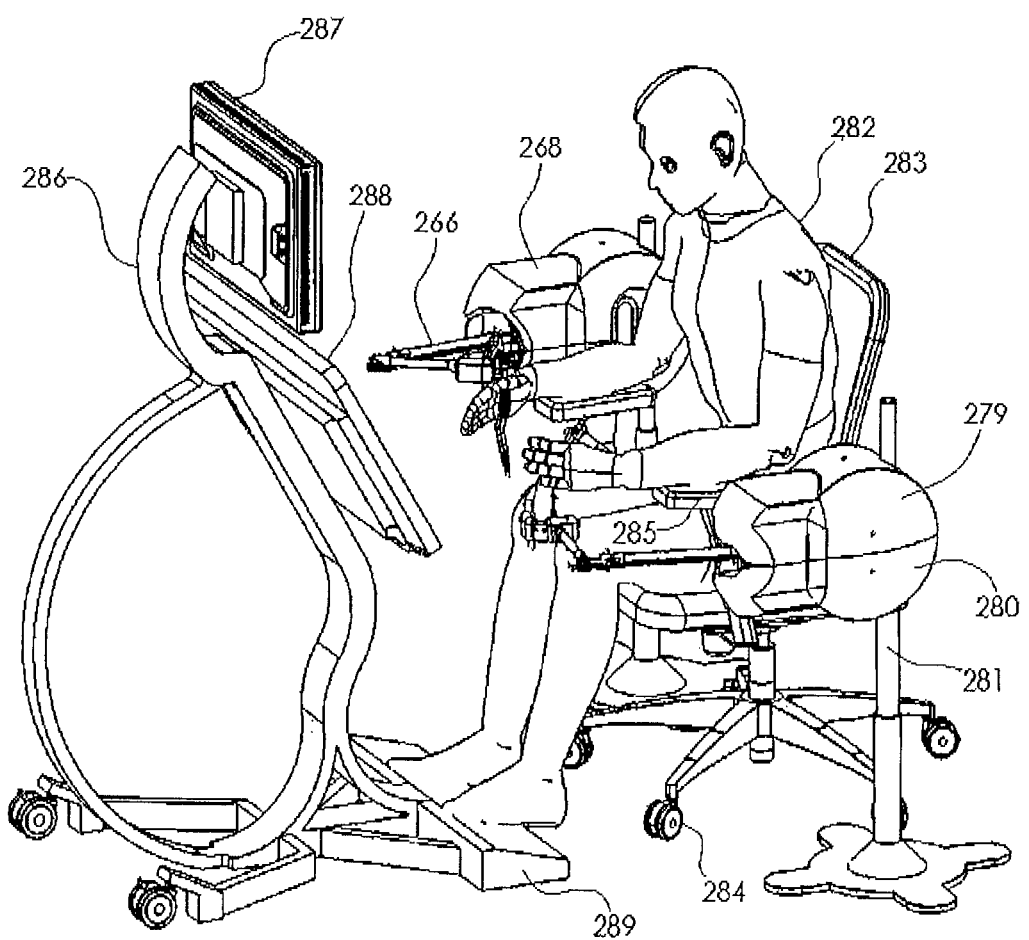
FIG. 8 illustrates a system for remote microsurgery including the local haptic hand controllers of FIG. 6 and FIG. 7 and further including associated devices.

FIG. 8 illustrates a system for remote microsurgery including the local haptic hand controllers of FIG. 6 and FIG. 7 and further including associated devices. In an embodiment, the surgeon or operator can operate, using the local haptic hand controller, both a right hand remote surgical tool and left hand remote surgical tool, using similar local surgical tools as at the remote site. Using two local haptic hand controllers together, such as the example embodiment in FIG. 6 configured for right hand use and the example embodiment of FIG. 7 configured for left hand use, the operator can have both right and left hands operating at the same time, which most resembles regular surgery. Even if one of the hands is free, the surgeon often prefers to use their left hand to operate a portion of the remote robotic manipulator to support the operating right hand, similar to how the surgeon would perform the surgery locally.

The system shown in the example embodiment of FIG. 8 is configured to meet large dexterous workspace, structural link length criterion within the whole workspace, and high integrated conditioning index (ICI). Embodiments of the present disclosure specifically meet the structural link length criterion within the whole workspace, while maximum manipulability and isotropy have been considered to achieve a desirable kinematic performance. Embodiments of the present disclosure concern an ergonomic system to provide comfort and flexibility for different operators and preferences. In an example embodiment, the system includes a base which supports the hand controller and allows for adjusting at least two additional degrees of freedom.

Embodiments of the present disclosure enable the operator or surgeon to either be seated or standing. A seated implementation is shown in FIG. 8. A standing implementation can be achieved using the configuration shown in FIG. 4, or a similar setup. As shown in FIG. 8, the end-user/surgeon 282, sits In a chair 283 with wheels 284 with the operator's upper limb rested on arm rests 285 and viewing the remote surgical site on the monitors 287, 288 installed onto a workstation console 285. One hand-controller or bimanual hand-controllers (attached to a fixed or adjustable base) is/are placed on one or both side(s) of the end-user/surgeon 282. In an embodiment, the end-user/surgeon 282 activates the remote robot manipulator through a tele-operative haptic-feedback network via a foot pedal 289 attached to the workstation. The system of FIG. 8 includes additional components that enable the operator to have a 3D view of the operating site, such that the surgical workstation is as informative/immersive as possible. For example, a pre-operative scan can be displayed on one monitor, and lab information can be displayed on another screen.

The example embodiment of FIG. 8 shows compact operation with at least one monitor. In an embodiment, one monitor shows the virtual reality of the remote manipulator, and the other one would show additional data, surgical zone, back view of the robot. In an example embodiment, the display provided directly in front of the surgeon is the work site, with the image being provided by the microscope camera at the remote robotic manipulator. Such an example implementation provides depth perception and a high resolution image, enabling the surgeon to operate while looking at the primary monitor. The other monitor can show related information, such as a pre-op scan, vascular imaging, etc.

Figure 9:
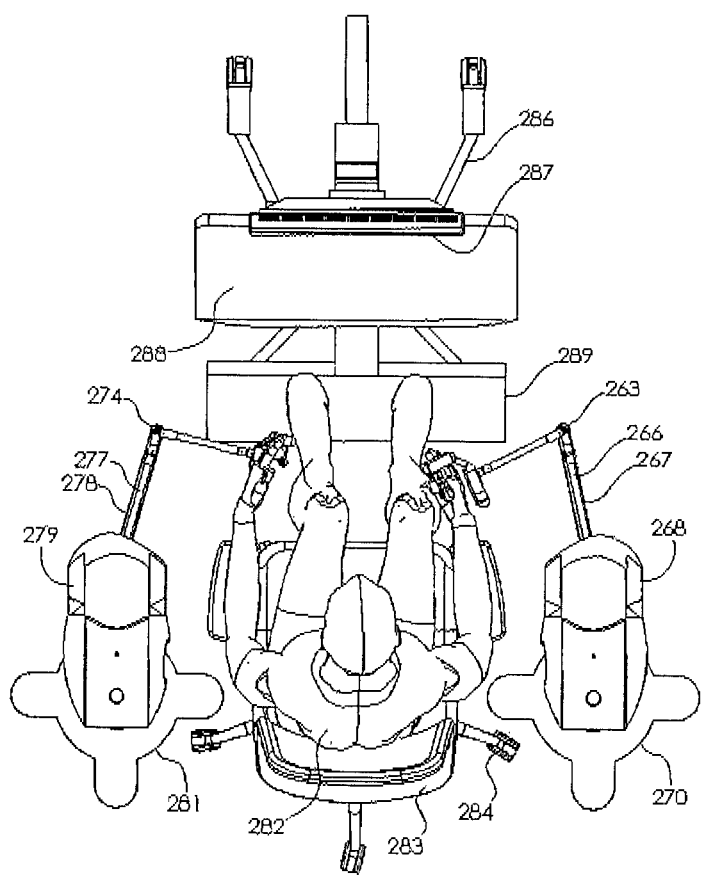
FIG. 9 is a top view of the system of FIG. 8, which illustrates the operator right arm movement shown in FIG. 3.

FIG. 9 is a top view of the system of FIG. 8. The view in FIG. 9 provides an additional perspective on the location of the operator with respect to the two local haptic hand controllers in this example implementation. FIG. 9 also illustrates, in context, the operator right arm movement shown in FIG. 3, namely translating operator arm movement into movement of at least one of the plurality of linkages in the kinematic structure in a direction parallel to and side-by-side with the operator arm movement.

Figure 10:
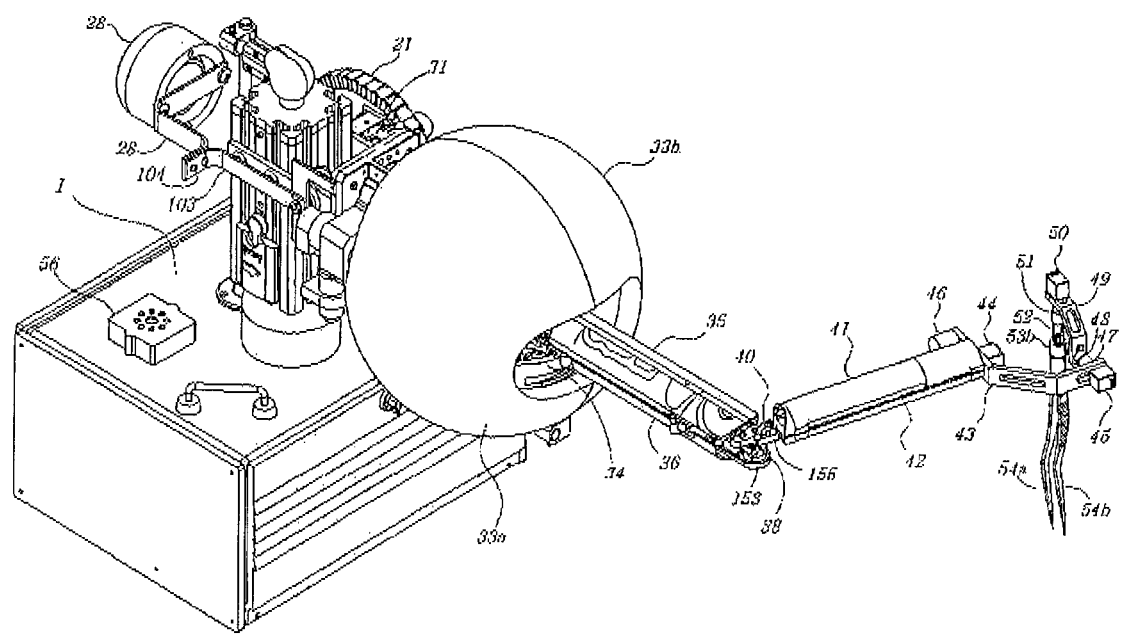
FIG. 10 illustrates a local haptic hand controller according to another embodiment of the present disclosure including a spherical casing surrounding a portion thereof.

FIG. 10 illustrates a local haptic hand controller according to another embodiment of the present disclosure including a spherical casing surrounding a portion thereof. The spherical casing includes a first casing portion 33*a* and a second casing portion 33*b*. In an example embodiment, the kinematic structure comprises an articulated structure including a plurality of serial linkages, the articulated structure having at least three positional degrees of freedom, and at least four force degrees of freedom. In an example embodiment, the kinematic structure comprises a shoulder assembly, and the spherical casing is configured to cover the shoulder assembly. In an example embodiment, the local haptic hand controller comprises at least nine positional degrees of freedom, and at least three degrees of freedom force feedback.

As shown in FIG. 10, in an example embodiment, the kinematic structure comprises at least one linkage arm having at least three translational degrees of freedom to replicate human elbow and shoulder motion. In an example embodiment, the kinematic structure comprises at least one linkage arm comprising at least three actuators installed on the linkage arm to provide at least 3 degrees of force feedback. In the example embodiment of FIG. 10, the kinematic structure comprises an upper arm assembly and a lower arm assembly.

The example embodiment of FIG. 10 shows an example embodiment in which the gimbal comprises a 4-DOF positional feedback RRR (three revolute joints) type gimbal. The gimbal is connected to the forearm assembly to provide the required local pitch, roll and yaw degrees of freedom to enable the local haptic hand controller to mimic the elbow-wrist-finger motions of the operator in 3D space. The gimbal as shown in FIG. 10 has been designed such that the tool is grabbed and held from the top end, thus the gimbal frame stands above the operator's hand. Based on this design, force application to a virtual target in 3D space is carried out by pulling the tool-gimbal connection point toward the target. An advantage of this. configuration is that the tool is thoroughly free of any extra attachment, except the top dome, which is not used during a surgery. In an example embodiment, the gimbal size, weight, mass inertia, stiffness, dexterity, umber of supports and components are selected to provide a better sense of maneuverability.

In the example embodiment of FIG. 10, the gimbal comprises a large link (G-L-Link) 43, large link encoder (G-L-Encoder) 44, small link (G-S-Link) 49, small link encoder (S-L-Encoder) 45. The local surgical tool comprises two prongs 54*a*,54*b*, and a tool encoder (G-T-Encoder) 50 configured to encode the tool with a unique tool identifier, such as a tool type identifier or an individual tool identifier. The gimbal further comprises a tool holder set 53*b* with corresponding portion (not shown), electric cylindrical connector 52, sleeve coupling (G-S-Coupling) 47, threaded stud 48, tool connector sleeve coupling (G-TC-Coupling) 51, and a counter balance weight (G-C-Weight) 46. In an example embodiment, three rotary encoders 44,45,50 are used to measure the local pitch, yaw, and roll angles of the gimbal joints. In an implementation, each encoder 44,45,50 is equipped with internal ball bearing supports (not shown), multi-purpose pins, and low friction torque, besides ignorable axial and radial play. The freely rotating shaft of the G-L-Encoder 44 pivots the G-L-Link 43, such as through a male/female push-pull connection (Joint IV).

The connector 52 allows for swapping different surgical tools including single-prong tools, e.g., suction tube, surgical dissectors, or laser head, and dual-prong ones, e.g., bipolar forceps, micro scissors, or tweezers. Implementation of sensorized tools, such as the ones equipped with magnetic or Hall effect sensors, flow rate sensors, pressure sensors, and force sensors, is of high importance for a microsurgery-specific haptic hand controller. Regarding the dual-prong surgical tools, the controller is able to measure the variable distance between two prongs 54a,54b when performing a task by, for example, utilizing a set of Hall effect sensor and permanent magnet installed oppositely on the inner surfaces of the two prongs. Therefore, the operator is able to control the opening/closing status of the corresponding actuator installed on the slave robot in an analogue open or closed loop.

Figure 11:
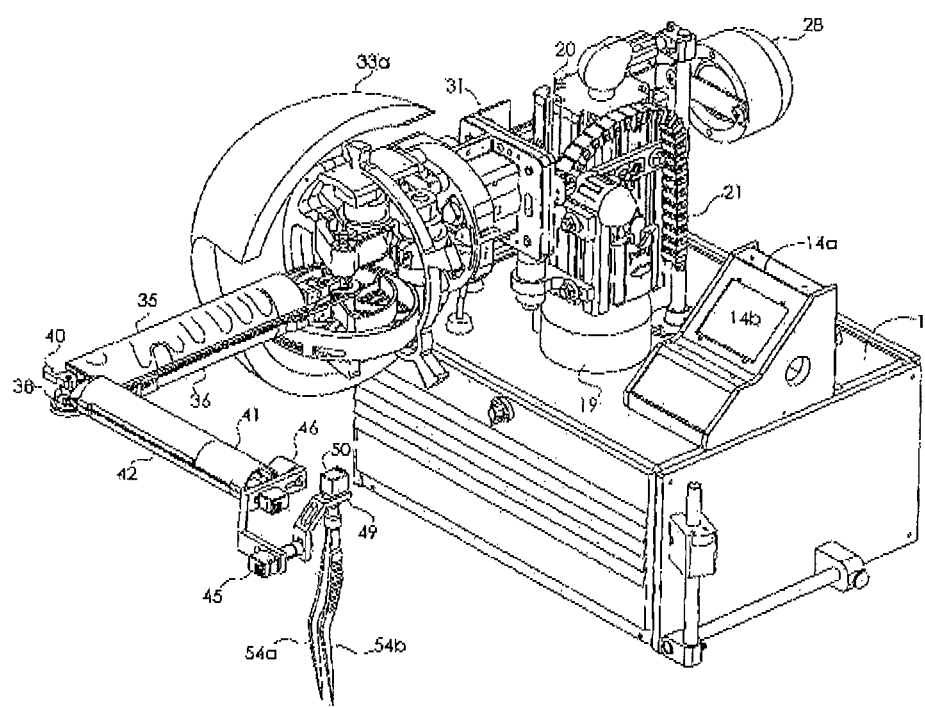
FIG. 11 illustrates another view of the local haptic hand controller of FIG. 10 with part of the spherical casing removed.

FIG. 10 and FIG. 11 are isometric views of a microsurgery-specific local haptic hand controller according to an example embodiment of the present disclosure showing most of the assembled components including the adjustable base, control box, control panel, shoulder, elbow I, elbow II and gimbal joints, arm, forearm, and gimbal links, tool and tool attachment, calibration module, electrical measurement instruments, and counter balance weight. As shown in the example embodiment of FIG. 10 and FIG. 11, one or more portions of the local haptic hand controller can be covered, such as by enclosures 33a, 33b, detachable lower arm covers 41 and 42, detachable upper arm covers 35 and 36. The local haptic hand controller as illustrated in this example also includes a stopper shim block 40, a power transmitter (such as a t-pulley) 38, and pillow blocks 153 and 155. As shown in the example embodiment of FIG. 10 and FIG. 11, the base stand is a control box (CBOX) 1. The adjustable base comprises at least two combined (rotational and/or prismatic) degrees of freedom; the base joints are of type prismatic-joint (P type), revolute pan joint (R type), and/or tilt joint (R type), said PR, RR, or PRR. The changes in the height and angles of the base joints are applied, either indirectly (manually by means of mechanical elements installed, on the workstation console or the base) or directly (by means of a touch screen) by the user.

In an embodiment, CBOX 1 accommodates a main controller, a power supply, On/Off toggle key, data acquisition board (DAQ), drivers, cables and all other elements connected to the main controller. A dome-shaped housing, or shading foot, 19 (shown in FIG. 11) is fixed on the CBOX 1. A pan driving assembly 21 is settled on the CBOX on top of the shading foot by fixing the bottom motor end cap, such as by using a bolt and nut. In an embodiment, a square profile spacer is laid in the interior space of the shading foot 19 underneath the bottom motor end cap to adjust the height of the pan assembly. A Pole 20, which can include versatile quick connectors, is used to build a pan mechanism.

In an embodiment, a force resistive sensor (FSR) is provided in a sensor casing fixed to the right sides of the pole. In an embodiment, a similar sensor casing is also attached to the left side of the pole 20. The sensors are pushed by the operator to spin the pole (pan motion) to the right or left.

Attached to the front side of the pole 20 is a tilt mechanism comprised of an actuator which is itself assembled with a gearhead—similar to what is used for the pan motion—an additional gearbox made of a bevel gear set (spur bevel, spiral bevel, zerol or hypoid), a tilt plate, tilt shaft, tilt potentiometer, counter balance weight 28, two lateral rectangular bar links, a couple of intermediate lift arms and a few holding brackets. The tilt actuator shaft, upon which a bevel pinion is mounted, transmits the power to a bevel crown gear on the tilt shaft.

A central pocket machined in the tilt plate allows the cables/wires to pass towards the cable chain 21. The cable chain 21 is attached to the right side of the pole 20 and moved up and down, synchronously, with the tilt plate 31. By launching the tilt mechanism, a tilting geared actuator will energize the shaft via the additional external gearbox and therefore, the tilt lifting arms will rotate the tilt plate 31 while having been supported by a set of counter balance weight 28 hung from the back of the pole 20 far behind the tilt axis.

A titling geared actuator Is secured to the pole 20, for example using two upper and lower fixtures and T-bolt versatile quick connectors. The lower fixture keeps the tilt geared actuator from any unwanted pivoting about the upper T-bolt central axis. A rotary positioning sensor (e.g., potentiometer, encoder, resolver, etc.) is coupled to one end of the tilt shaft, for example through a nut and tilt coupling.

FIG. 11 illustrates another view of the local haptic hand controller of FIG. 10 with part of the spherical casing removed. The example embodiment illustrated in FIG. 11 shows components of the shoulder assembly, which will be described in further detail in relation to FIG. 12. FIG. 11 also illustrates a human-machine interface (HMI) or graphical user interface (GUI) 14a, comprising a display screen 14b. In an example embodiment, the HMI comprises a touch-based computer controlled system installed on the CBOX 1 beside the pole 20, or on the monitoring console in front of the operator, including a touch screen display 14b. The HMI is configured to enable the operator to control the moving speed of the base through the GUI and is able to use a HOME function to send the base to a known, or stored, home position when needed. In an example embodiment, the HMI or GUI also comprises a sound system to record and play, such as via a speaker 56 shown in FIG. 10, guiding voice messages for the novice operators who are not familiar with the device and walk them through all the adjustment procedures, step-by-step.

Figure 12:
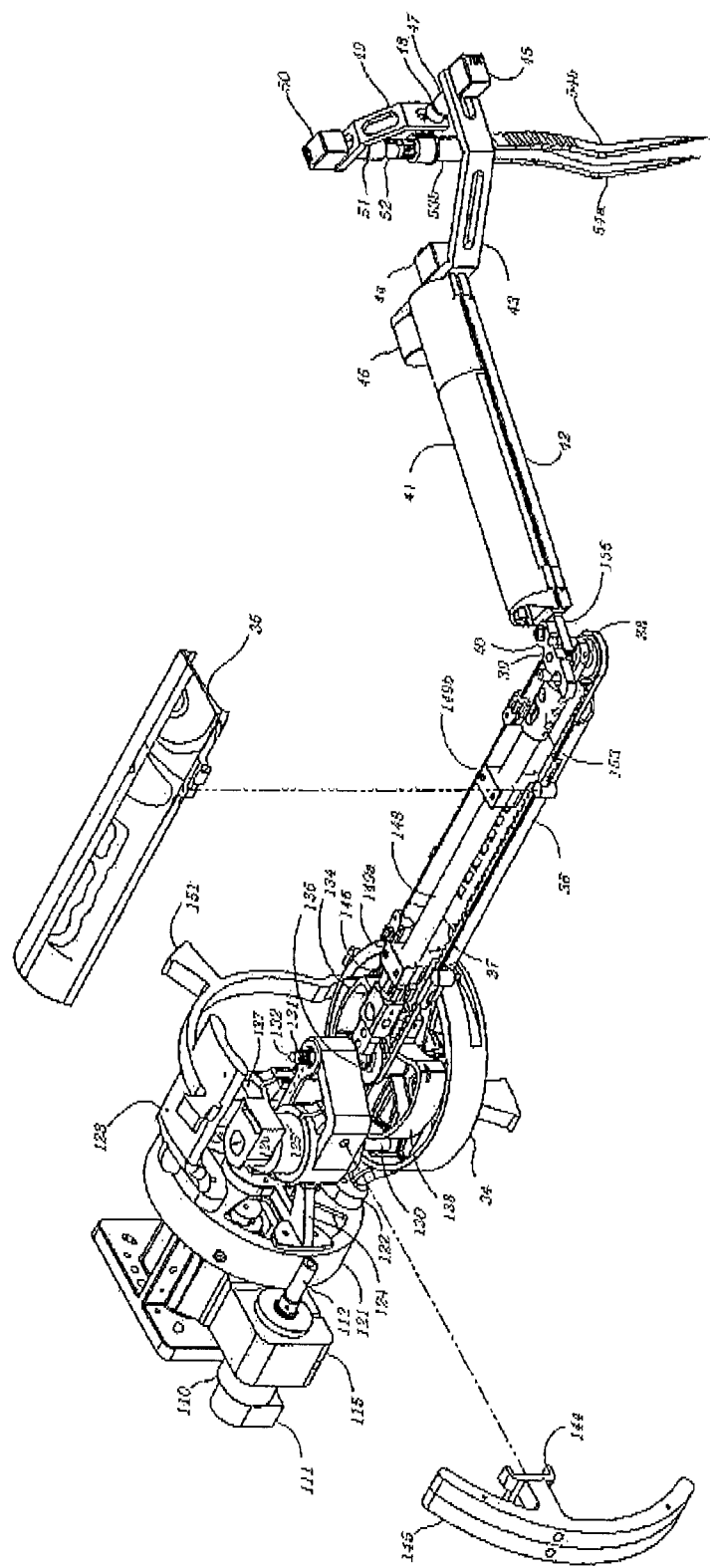
FIG. 12 illustrates a detailed view of a kinematic structure of a local haptic hand controller according to an example embodiment of the present disclosure.

FIG. 12 illustrates a detailed view of a kinematic structure of a local haptic hand controller according to an example embodiment of the present disclosure. In an example embodiment, the kinematic structure comprises a shoulder, or a shoulder assembly, which facilitates a flexion/extension degree of freedom for the operator for physically exchanging at least one component of a 3-dimensional force vector with an operator's hand/finger. In an example embodiment, such as shown in FIG. 12, the kinematic structure comprises two links and two joints which facilitate both the abduction/adduction and internal/external rotational degrees of freedom for physically exchanging at least two components of a 3-dimensional force vector with an operator's hand/finger.

In the example embodiment of FIG. 12, the two links comprise an upper arm and a forearm, and the two joints comprise an upper elbow joint provided at a first end of the upper arm, and a lower elbow joint provided between a second end of the upper arm and the forearm. In an example embodiment, the kinematic structure comprises: a shoulder assembly; an upper arm pivotally connected to the shoulder assembly; a lower elbow joint pivotally connected to a lower end of the upper arm; and a forearm pivotally connected to the lower elbow joint, and the gimbal is pivotally connected to the forearm. In an example embodiment, the shoulder assembly comprises: a rotary joint; and an upper elbow joint coupled to the rotary joint.

In an example embodiment, the local haptic hand controller further comprises; a lower pulley actuator provided in the upper elbow joint; an upper pulley provided in the upper elbow joint; and a power transmission device in communication with the upper and lower elbow joints and configured to transmit power from the lower pulley actuator in the upper elbow joint to an axis of the lower elbow joint v the upper pulley. In an example embodiment, the kinematic structure is adapted to exert forces and/or torques for at least partial compensation of gravity related forces. In an example embodiment, the kinematic structure is adapted to exert torques acting in at least one of three translational degrees of freedom.

In an example embodiment, the kinematic structure. comprises a shoulder, an upper arm and a forearm, and further comprises actuators configured to power three independent freedoms of the upper arm and the forearm relative to the shoulder to provide the at least partial gravity compensation.

Describing the embodiment of FIG. 12 in further detail, in an example embodiment, a 3-DOF serial linkage mechanism, configured to mimic the human upper limb motion, is mounted on the base. The serial linkage mechanism in this example embodiment includes a shoulder, two elbows (upper elbow joint, or elbow I; and lower elbow joint, or elbow II), four power transmitters and a linkage arm itself comprised of arm and forearm assemblies. The shoulder includes a rotary joint (joint I) comprised of an 8-Actuator 110, S-Encoder 111, threaded capstan (S-Capstan) 112, drum (S-Drum) 121, rope (S-Rope), S-Axle, and a housing (S-Housing) 115 to hold the S-Actuator 110, and all the aforementioned components of the shoulder assembly. In a first design with an adjustable base, S-Housing 115 is flush mated onto the tilt plate 31 shown in FIG. 10, for example using four sets of bolts and nuts-washers. The S-Actuator 110, S-Capstan 112, S-Drum 121 and S-Rope, wrapped around the capstan/drum set, constitute the rotational joint entity of the shoulder mounted on the S-Axle 119. The output power of the S-Actuator 110 is transmitted through the S-Capstan 112 (seated on the rotary actuator shaft) to the shoulder axis of rotation (S-Drum center axis) through the S-Rope.

The rope is crimped/tightened at both ends to the drum 121 and the rope tension is adjustable benefiting from a holt-nut tensioning method. In an embodiment, each actuator 110,125, or 127 comprises an encoder configured to measure the movement angles of the joint I, joint II (elbow I) and joint III (elbow II), in real time.

Two concentric joints, referred to as elbow I (joint II) and elbow II (joint III), are assembled to the shoulder assembly. All the elbow components are mounted on the S-Drum 121 top surface, Each elbow joint is comprised of a rotary actuator (E1-Actuator 127 and E2-Actuator 125), encoder (E1-Encoder 128 and E2-Encoder 126), threaded capstan (E1-Capstan 129 and E2-Capstan 130), drum (E1-Drum 34 and E2-Drum 138), and rope (E1-Rope and E2-Rope) (not shown), similar to S-Actuator 110, S-Encoder 111, S-Capstan 112, S-Drum 121, and S-Rope, respectively. In an embodiment, the shoulder and elbow actuators are connected to driving carriers (not shown), embedded inside the CBOX 1. The drivers are used to sense the actuator currents and feed/control actuators based on pulsed width modulation (PWM) or other relevant techniques. They also measure the currents taken by the actuators.

In an embodiment, a connector such as a 20-pin tiny plug connector is paired with a lock-type receptacle, Which carries all the signals between the adjustable base (control cabinet, not shown) and the sensors/encoders an the linkage arm and the gimbal. This connector also facilitates disassembling of the modular haptic device.

A pillar block (1-PBlock I) 134 connects the arm link (Link I) 148 to the E-Shaft 132. The E-Shaft 132 has been constrained coaxially to the E-Pillar 124. E1-Drum 34 is fixed to the E-Shaft 132 through a couple of set screws on the drum hub and rotates synchronously with the arm assembly. A semi-circular collar is hinged to the both L-shaped stands 122,123 to be used as an adjustable support for the two covering semi-globes 33a,33b. Those two semi-globes 33a,33b are mounted on the collar 151 symmetrically to cover the shoulder-elbow assemblies. Mounting position of all the shoulder and elbow components was designed symmetrically around the S-Drum 121 to reduce the gravity effects. However, a counter balance weight 145 is added to the E-Pillar 124 through a U-shaped mount block 144 to compensate the mass of the whole structure. E2-Drum 138 is able to freely rotate around the E-shaft 132 axis via a ball bearing support 139 embedded concentrically within the central drum bore. A pillow block (A-PBlock I) 134 connects the arm link (Link I) 148 to the E-Shaft 132. E1-Drum 34 is fixed to the E-Shaft 132 through a couple of set screws on the drum hub and rotates synchronously with the arm assembly.

The arm assembly is composed of an arm link (Link I) 148,266, two pillow block supports (A-PBlock I) 134,365 (A-PBlock II) 153, arm upper cover (A-U-Cover 35,292), arm lower cover (A-L-Cover 36,) two timing pulleys (T-Pulley I 136, and T-Pulley II 38,), one timing belt strand 37.

The arm assembly is composed of an arm link (Link I) 148, two pillow block mount supports (1-PBlock 1134 and 1-PBlock II 163), detachable arm upper cover (1-U-Cover 35), detachable arm lower cover (1-L-Cover 36), two timing pulleys (T-Pulley I 136 and T-Pulley II 38), one timing belt strand 37, one button side stop pin 154, compression steel spring 152, elbow rod (E-Rod) 39 as the center of transmitted rotational motion for the elbow II, clamps and stands 146,147,149a,149b

A flexible backlash-free transmitter (e.g., a timing belt or synchronous chain) 37 transmits the power needed to activate the forearm assembly between the center axis of E-Shaft 132 and E-Rod 39. A timing pulley/sprocket (T-Pulley I) 136 is coaxially fixed to the E2-Drum 138 through a hub coupling 137 with assistance of a few set screws (not shown) and spins on the E-Shaft 132 using a ball bearing 135. A similar timing pulley/sprocket (T-Pulley II) 38 is fastened onto the E-Rod 39 through fixing two set screws located on the hub. A ball bearing 156 is press fitted Inside the pocket of 1-PBlock II 153 considering a tight tolerance (e.g., $ℓ^{0}_{-0.01}$). E-Rod 39 supported by 1-PBlock II 153 freely rotates with the inner ring of the bearing. The 1-L-Cover 36 is coupled to the Link I 148 using two split-muff clamps 149a,149b, and screws 150. Then the 1-U-Cover 35 will be paired onto its lower peer by a cam clamping method.

Figure 13:
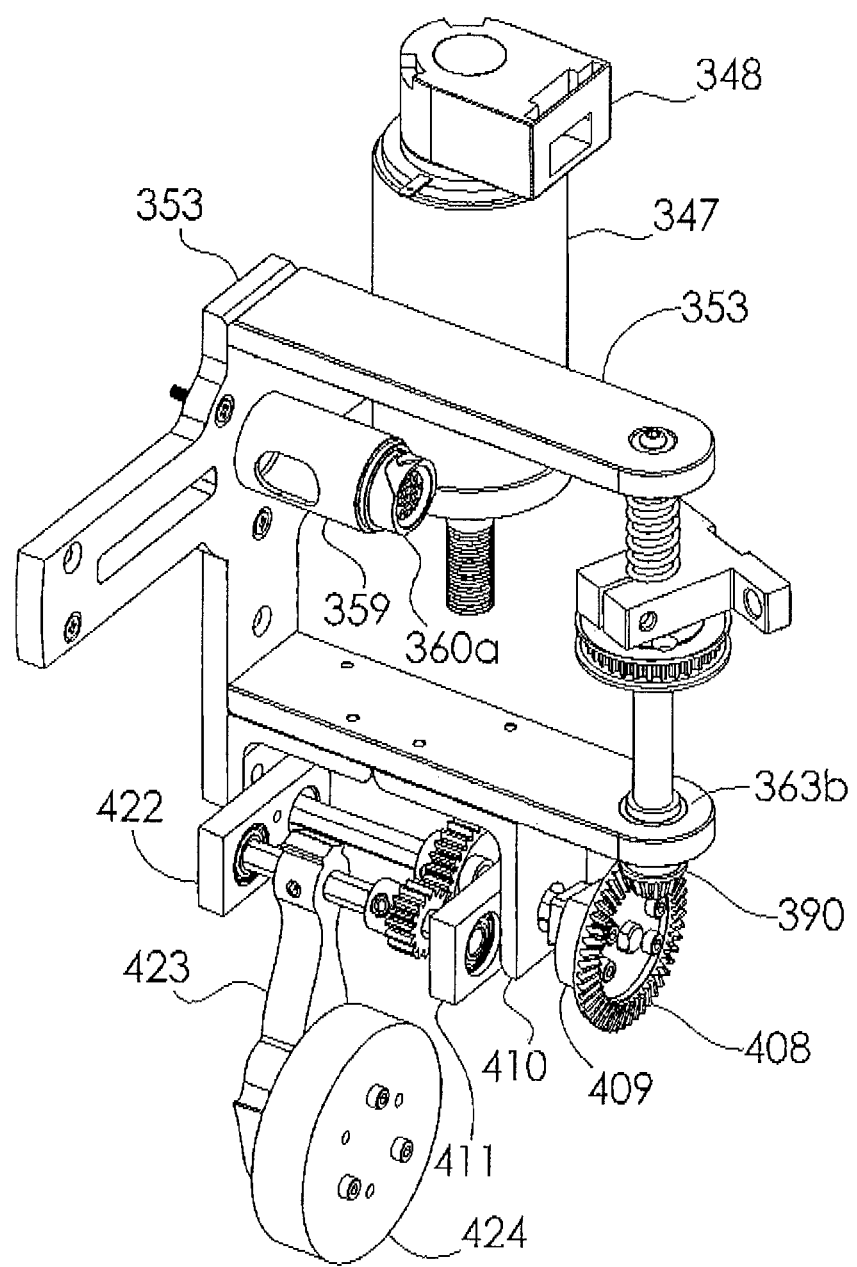
FIG. 13 illustrates a static counterbalance mechanism for use with a local haptic hand controller according to another embodiment of the present disclosure.

FIG. 13 illustrates a static counterbalance mechanism for use with a local haptic hand controller according to another embodiment of the present disclosure. The static counterbalance in FIG. 13 is connected directly or indirectly to the linkage arm. If the static counterbalance is removed, the gravity compensation of the device may not be desirable. In an example embodiment, the static counterbalance comprises all of the elements below the bracket 363b.

As shown in FIG. 13, the hand-controller takes advantage of a gear-in-mesh static counterbalance connected indirectly to the arm joint/link (Joint II) through the U-shape elbow support frame 353 and the bevel gear 390. A counter weight 424 swings towards or against the shoulder axis to compensate for the hand-controller gravity force. The bevel gear 390 is in mesh with a larger bevel gear 408, The gear 408 is secured to a shaft, for example by means of a locking bracket 409 and four screws. Two shafts and are placed in parallel, housed by two flat machined plates 411 and 422 via bearings. The plate 411 shown in FIG. 13 is mated with an L-angle bracket 410. A pinion transmits the rotational motion from a first shaft (gear) to a second shaft, on which it is seated. A pendulum 423, which is fixed to the shaft, secures the counterweight 424. Therefore the counterweight 424 swings around the shaft axis. The pinion and gear reduce the resistant/inertia that the user might feel due to the back drivability of the counterweight 424. This system also helps have the counterweight 424 as close as possible to the base. The bevel gear 408 also magnifies the transmission ratio to have larger scale of motion on the counterbalance. In an implementation, the gear-in-mesh static counterbalance is stiffened to a lower support bar of the U-shape elbow support frame 353 by virtue of two L-angle brackets and fasteners.

FIG. 13 also illustrates an actuator 347 and an encoder 348. A central tube 359 can be provided on the support frame 353, with a connector 360a (such as a 20-pin tiny plug connector) paired with a lock-type receptacle.

Figure 14:
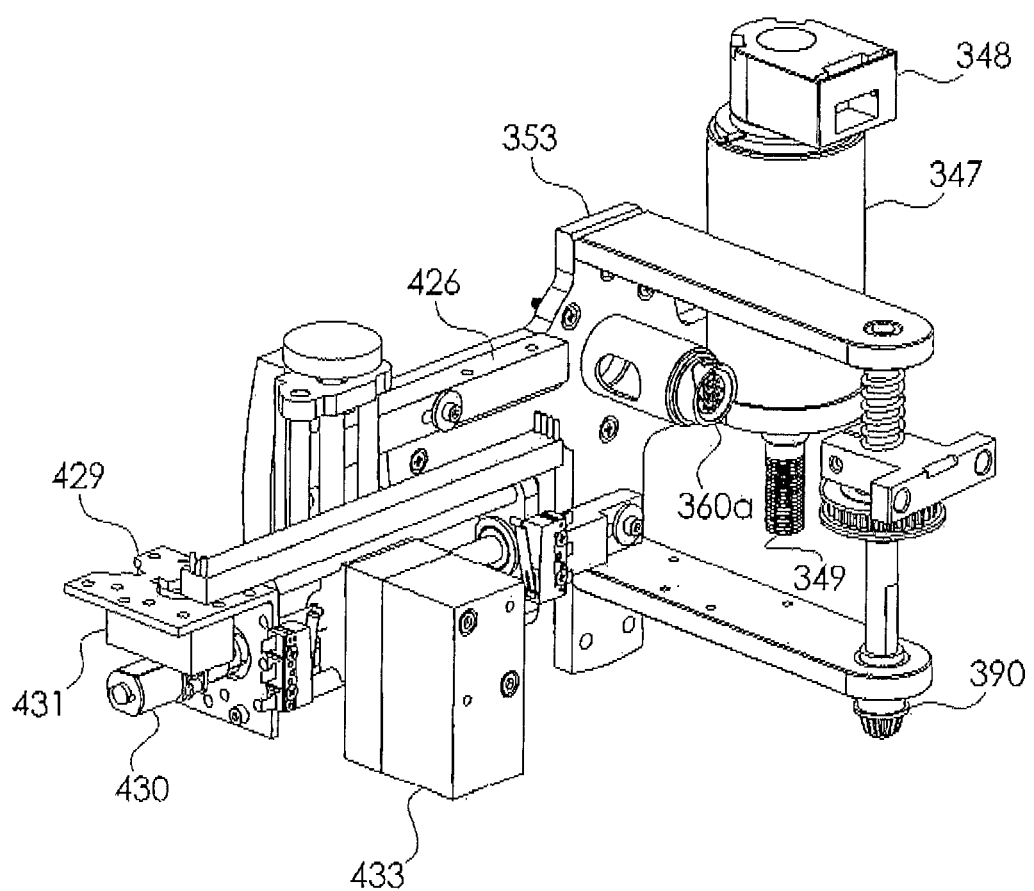
FIG. 14 illustrates a dynamic counterbalance mechanism for use with a local haptic hand controller according to another embodiment of the present disclosure.

FIG. 14 illustrates a dynamic counterbalance mechanism for use with a local haptic hand controller according to another embodiment of the present disclosure. The motorized dynamic counterbalance in FIG. 14 is an optional element that can improve counterbalance performance. This motorized dynamic counterbalance is different from the non-motorized dynamic counterbalance provided by element 145 in FIG. 10, which is very simple and is a simple piece of metal, which is generally banana shaped.

As shown in FIG. 14, the hand-controller in this example embodiment takes advantage of a motorized dynamic counterbalance attached to a cross-shape holder of a U-shape elbow support frame 353 through a horse-shoe support 426. The dynamic counterweight 433 moves towards or against the shoulder axis automatically by changing the location of the hand-controller center of gravity (CG). In an example embodiment, the dynamic counterbalance comprises a vertical motion compartment responsible for moving the counterbalance stage up and down manually. In an embodiment, the dynamic counterbalance comprises a horizontal motion compartment responsible for moving the counterbalance stage right and left, automatically. The counterweight is also stiffened to the carriage, for example via screws. An L-angle bracket 429 accommodates a gear-motor 430 and a spacer block 431. In an example embodiment, the gear-motor 430 receives signals from the control software, energizes a leadscrew through a coupler and thus moves the counterweight 433. In an example embodiment, the dynamic counterbalance assembly comprises: a dynamic counterweight; a gear motor in communication with the control system and coupled to the dynamic counterweight. The gear motor is configured to move the counterweight in response to a dynamic counterbalance signal received from the control system.

Figure 15:
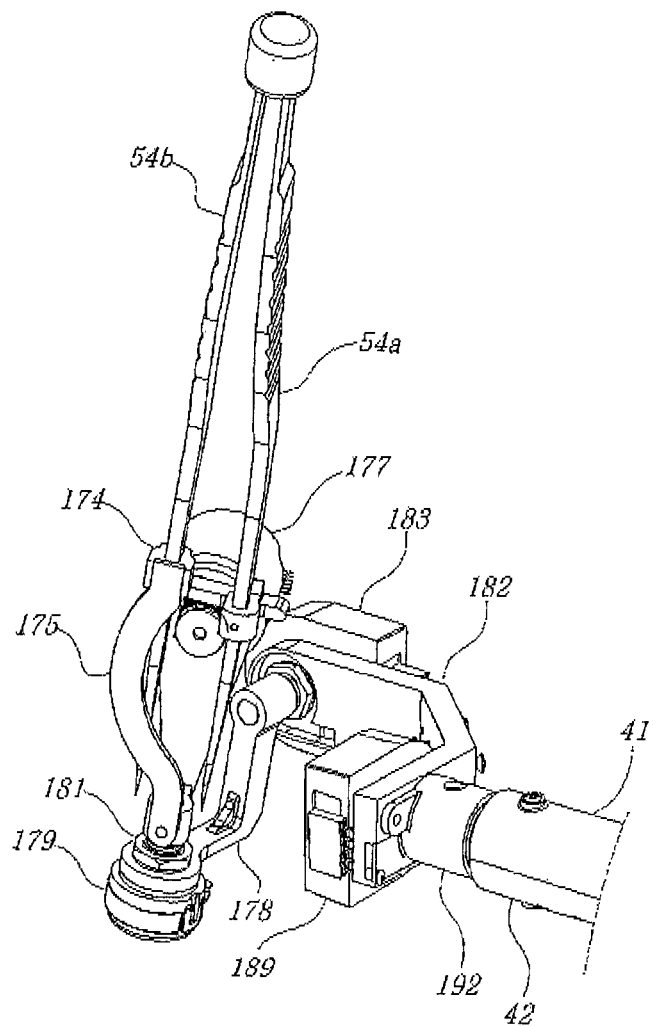
FIG. 15 illustrates a gimbal of a local haptic hand controller according to an embodiment of the present disclosure for use with a dual prong surgical tool.
Figure 16:
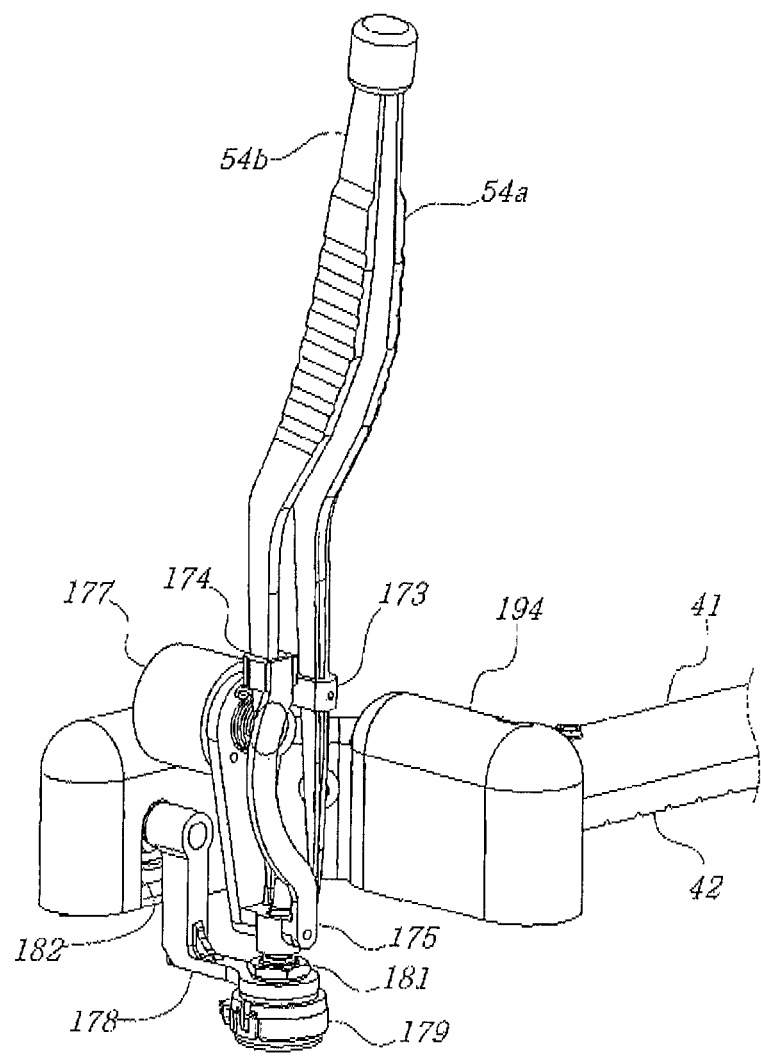
FIG. 16 illustrates a gimbal of a local haptic hand controller according to another embodiment of the present disclosure for use with a dual prong surgical tool.

FIG. 15 illustrates a gimbal of a local haptic hand controller according to an embodiment of the present disclosure for use with a dual prong surgical tool. FIG. 16 illustrates a gimbal of a local haptic hand controller according to another embodiment of the present disclosure for use with a dual prong surgical tool. In an embodiment, the gimbal in FIG. 16 is the same as the gimbal of FIG. 15, but with protective covers shown in FIG. 16, and removed in FIG. 15 to show internal components.

The gimbal of FIG. 15 and FIG. 16 is configured such that the tool is attached to and held at a mid-point of one prong of a dual prong surgical tool; thus the gimbal frame stands underneath the operator's hand. Based on this design, force application to a virtual target in 3D space is carried out by pushing the tool-gimbal connection point toward the target. The gimbal of FIG. 15 and FIG. 16 provides an opportunity to have an additional haptic force feedback in the tool level for dual-prong surgical tools, while neither being distractive nor obtrusive to perform an accurate surgery. In an example embodiment, the gimbal designed for dual-prong tools, e.g., bipolar forceps, has 4-DOF position sensing feedback and 1-DOF force-actuation feedback on the tool.

In an example embodiment, the gimbal of FIG. 15 and FIG. 15 is configured for attachment to a bipolar forceps 54, and is harnessed tightly by a miniaturized screw-driven clamp 174, leashed on the left prong 54b. In an embodiment, the miniaturized harness 174 is screwed or welded to the U-shaped support 175, and holds firmly the bipolar forceps 54. A rotary encoder 179, which measures the tool roll angle, is fastened to the lower side of the modified small link 178 of the gimbal, such as by means of a locking washer and jam nut 181. Then, the U-shaped support 175 can be tightened to the encoder 179 through a central hole drilled at the bottom. This hole is where the support 175 embraces the encoder shaft 179.

In an example embodiment, a geared small electric motor 177 is fixed to the U-shaped support 175. In an example embodiment, a miniaturized drum is provided on the part 173 in the shape of a circle sector, that can be meshed with a capstan, and produces a high-torque transmission system for the pinching-coagulation movements of the bipolar forceps 54. When the operator opens arid closes the prongs, the drum 173 will slide on the circumstance of the capstan with a small air gap in between; this generates a 1-DOF haptic force feedback directly on the tool to provide the operator with necessary data on how much force is being applied to the tissue at the remote robotic manipulator. In an implementation, the miniaturized drum 173 is screwed to the right prong 54a of the bipolar forceps. In an example embodiment, the tool 54 is also equipped with a position sensing sensor, which is accounted as the fourth degree of freedom for the gimbal.

A digital encoder 183 is configured to measure the gimbal yaw angle, and in an embodiment is connected to the upper side of the modified large link 182 of the gimbal. The G-S-Link 178 is fixed on the encoder shaft 183. The digital encoder 189 is fixed to the other side of the G-L-Link 182. A cylindrical housing 192 in which a ball bearing is hosted surrounds the encoder shaft 189 where the gimbal is considered to join the articulated linkage arm. In an example implementation as shown in FIG. 16, injection molded plastic coverage 194 is placed on top of the G-L-Link 182, and the bottom side can be covered by a plastic sheet. This cover is used to meet safety regulations and has the gimbal mechanics isolated from its surroundings.

In an example embodiment, the local surgical tool comprises at least one sensor in communication with the control system. In an example embodiment, the at least one sensor is selected from the group consisting of: a magnetic sensor, a Hall-effect sensor, an optical sensor, a strain-gauge resistive sensor, a piezo-electric sensor, a piezo-resistive sensor, a capacitive proximity sensor, and an induction sensor. In an example embodiment, the at least one sensor is configured to measure a distance between first and second prongs of forceps. In an example embodiment, the at least one sensor is configured to determine a force applied to the forceps by the operator based on the measured distance.

In an example embodiment, the local surgical tool comprises at least one actuator in communication with the control system. In an example embodiment, the at least one actuator is selected from the group consisting of: electric, electromagnetic, piezoelectric, pneumatic and hydraulic actuator. In an example embodiment, the at least one actuator is configured to provide high-definition force feedback to enable the operator to feel, at the local surgical tool, force applied to the remote surgical tool. In an example embodiment, the at least one actuator is configured to generate at least 1-DOF pinching or coagulating haptic force feedback between forceps prongs according to a real-time force applied to a tissue by the remote surgical tool.

Figure 17:
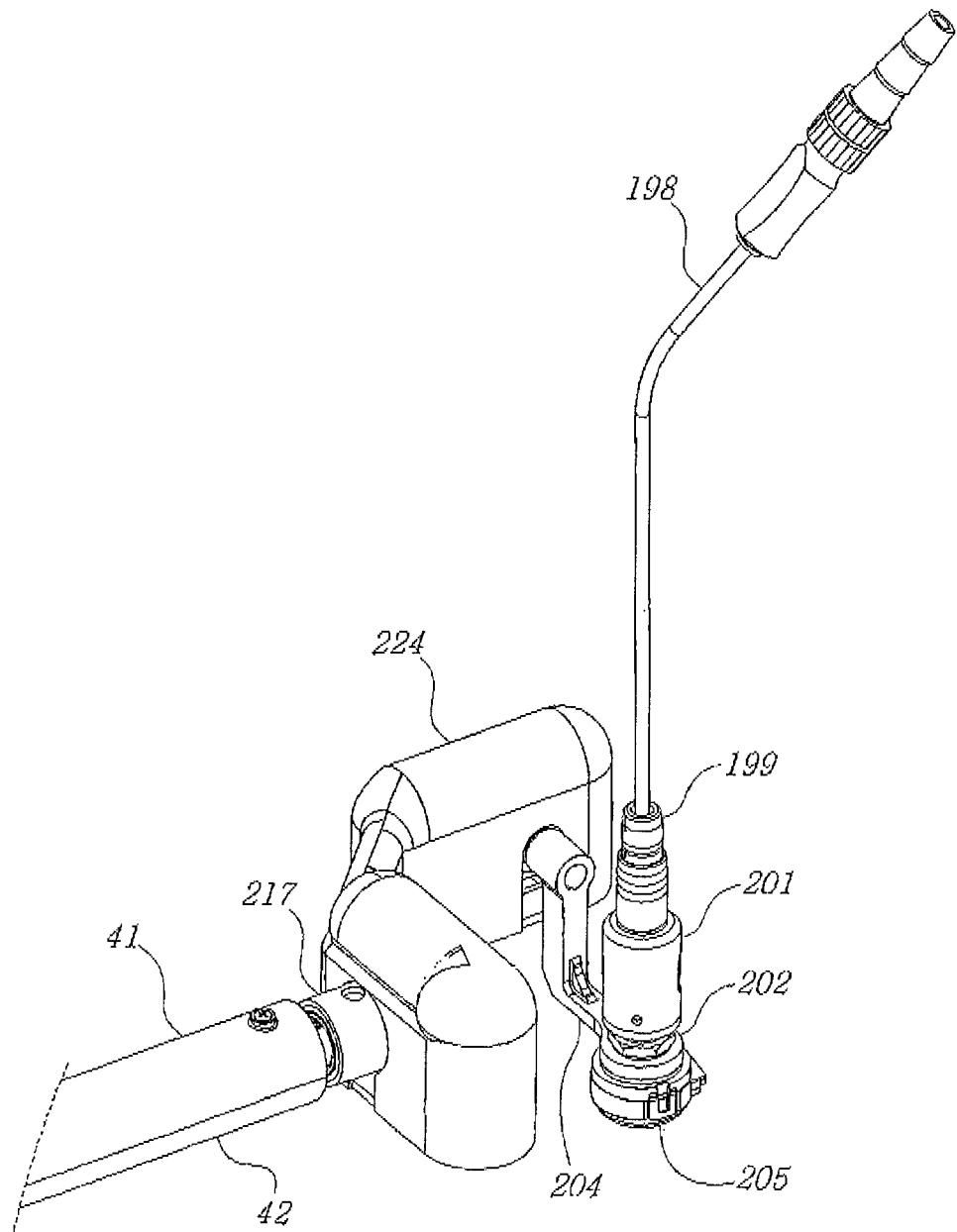
FIG. 17 illustrates a gimbal of a local haptic hand controller according to an embodiment of the present disclosure for use with a single prong surgical tool.
Figure 18:
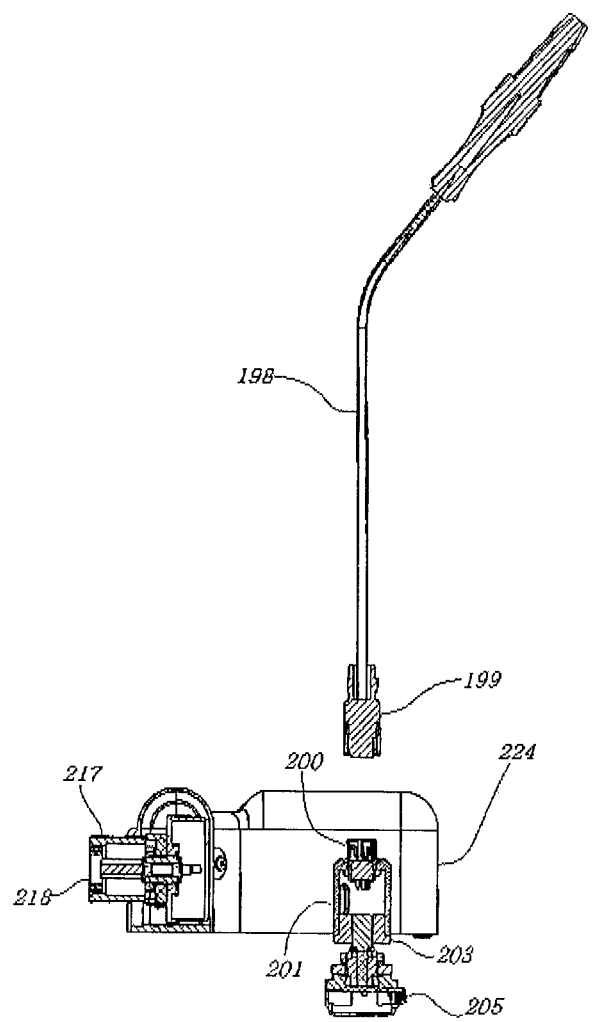
FIG. 18 illustrates a cross-section of a gimbal of a local haptic hand controller according to an embodiment of the present disclosure, similar to FIG. 18, for use with a single prong surgical tool shown detached from the gimbal.

FIG. 17 illustrates a gimbal of a local haptic hand controller according to an embodiment of the present disclosure for use with a single prong surgical tool, such as a suction device or surgical dissector. FIG. 18 illustrates a cross-section of a gimbal of a local haptic hand controller according to an embodiment of the present disclosure, similar to FIG. 18, for use with a single prong surgical tool shown detached from the gimbal.

As shown in FIG. 17 and FIG. 18, the tool 198 has a cylindrical end that fits in a connector 199 using a converter bushing (not shown). In an embodiment, a male connector 200 (shown in FIG. 18) is fixed to the modified small link 204 (shown in FIG. 17) of the gimbal, for example using a coupling set 201 and 203 as well as a jam nut 202. The tool is exchangeable and can be detached by disconnecting the male/female components of the push-pull locking connector 199,200. The gimbal comprises a roll measuring encoder 205 connected to the link 204. In another embodiment, the system also includes digital encoders configured to measure corresponding angles, and which can be fixed to a modified large link of the gimbal. A cylindrical housing 217 and other cover plates and coverage elements 224, such as plastic coverage, cover the wires and cables to improve operator safety while maintaining system functionality. A ball bearing 218 as shown in FIG. 18 facilitates the pitch motion (rotation around the encoder shaft) of the gimbal relative to the joined articulated arm.

Figure 19:
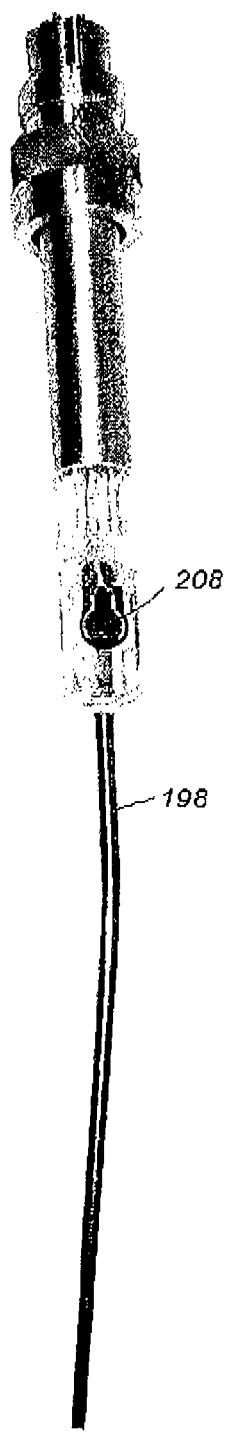
FIG. 19 is a top front perspective view of a single prong surgical tool for providing suction according to an embodiment of the present disclosure.
Figure 20:
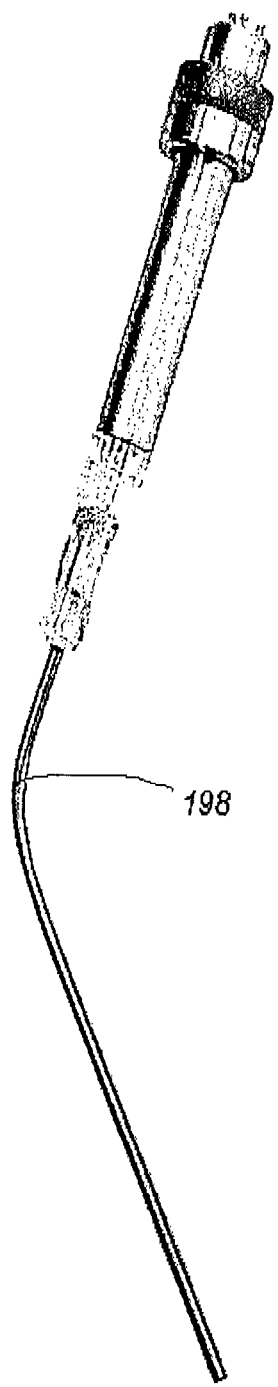
FIG. 20 is a side view of the single prong suction tool of FIG. 19.

FIG. 19 is a top front perspective view of a single prong surgical tool for providing suction according to an embodiment of the present disclosure. FIG. 20 is a side view of the single prong suction tool of FIG. 19. In an example embodiment, the local surgical tool 198 of FIG. 19 and FIG. 20 comprises a suction device including sensing actuator 208. The sensing actuator 208 is configured to: sense an amount of pressure applied by the operator to the sensing actuator; and control a flow rate of the suction device based on the sensed amount of pressure. As shown in FIG. 19, a sensorized encoded suction tool 198 is provided, which can be attached to the gimbal as shown in FIGS. 17 and 18. To enable attachment to the gimbal through the top end, in an example embodiment the tool comprises a tube, a handle bar, a force sensitive resistor (touch sensor) and a similar connector as used for the bipolar forceps in FIG. 15 and FIG. 16.

Embodiments of the present disclosure have thus far been described including the local surgical tool. Other embodiments are provided in which the local haptic hand controller is provided without the local surgical tool, which can be provided or purchased or obtained separately for interaction with the local haptic hand controller. In another embodiment, the present disclosure provides a local haptic hand controller for enabling an operator to remotely perform microsurgery by controlling a remote robotic manipulator, the local haptic hand controller comprising; a base, and a kinematic structure in communication with the base, the kinematic structure comprising a plurality of serial linkages and comprising a gimbal provided as an end-effector. The plurality of serial linkages and the gimbal cooperate, in use, to translate operator arm movement into movement of at least one of the plurality of linkages in a direction parallel to and side-by-side with the operator arm movement. A control system is in communication with a remote surgical tool and with a local surgical tool adapted for mating with the gimbal, the control system configured to enable operation of the local haptic hand controller when a local surgical tool identifier associated with the local surgical tool matches a remote surgical tool identified associated with the remote surgical tool.

In an example embodiment, the operator arm movement is caused by a first serial link chain defined by the operator's arm, and the plurality of linkages comprise a second serial link chain configured to move in parallel with, and together with, the first serial link chain. In an example embodiment, the kinematic structure comprises: a shoulder assembly including a rotary joint and an upper elbow joint coupled to the rotary joint; an upper arm pivotally connected to the shoulder assembly; a lower elbow joint pivotally connected to a lower end of the upper arm; and a forearm pivotally connected to the lower elbow joint, and wherein the gimbal is pivotally connected to the forearm.

Embodiments of the present disclosure have thus far been described including the control system. Other embodiments are provided in which the local haptic hand controller is provided without the control system, to which access can be provided separately, for integration and interaction with the local haptic hand controller. In a further embodiment, the present disclosure provides a local haptic hand controller for enabling an operator to remotely perform microsurgery by controlling a remote robotic manipulator, the local haptic hand controller comprising: a base; a kinematic structure in communication with the base, the kinematic structure comprising a plurality of serial linkages and comprising a gimbal provided as an end-effector, the plurality of serial linkages and the gimbal cooperating, in use, to translate operator arm movement into movement of at least one of the plurality of linkages in a direction parallel to and side-by-side with the operator arm movement, the plurality of serial linkages comprising: a shoulder assembly including a rotary joint and an upper elbow joint coupled to the rotary joint; an upper arm pivotally connected to the shoulder assembly; a lower elbow joint pivotally connected to a lower end of the upper arm; and a forearm pivotally connected to the lower elbow joint; the gimbal being pivotally connected to the forearm; and a local surgical tool provided at the gimbal and having a shape and construction substantially similar to a remote surgical tool provided at the remote robotic manipulator and with which the microsurgery is to be performed, the local surgical tool configured to communicate over the network with the remote robotic manipulator to control operation of the remote surgical tool based on operator movement of the local surgical tool.

Embodiments of the present disclosure have thus far been described primarily in relation to microsurgery and surgical tools. Embodiments of the present disclosure are also provided for other types of fine manipulation outside of microsurgery, such as fine manipulation of objects in a laboratory. For instance, a local haptic hand controller according to an embodiment of the present disclosure can be used to perform fine manipulation of laboratory objects at a remote location, for example in a quarantined area. In such an implementation, a remote fine manipulation tool is controlled by the local haptic hand controller, In an embodiment, the present disclosure provides a local haptic hand controller for enabling an operator to remotely perform fine manipulation by controlling a remote robotic manipulator, the local haptic hand controller comprising: a base; a kinematic structure in communication with the base, the kinematic structure comprising a gimbal provided as an end-effector; a local fine manipulation tool provided at the gimbal and having a shape and construction substantially similar to a remote fine manipulation tool provided at the remote robotic manipulator, the local fine manipulation tool comprising a local fine manipulation tool identifier; and a control system in communication with the local fine manipulation tool and with the remote fine manipulation tool, the control system configured to enable operation of the local haptic hand controller when a local fine manipulation tool identifier matches a remote fine manipulation tool identifier, In an example embodiment, an articulated structure is provided with at least 9 degrees of freedom (DOFs) including a fixed or an adjustable base (with at least 2 DOFs), an anthropomorphic linkage design structure (shoulder, elbow I and elbow II with at least 3 DOFs) and an end-effector (gimbal) a hand piece coupled with at least one single-prong and dual-prong surgical tool. Grabbing and maneuvering a surgical tool as the handgrip of the hand controller, in which the linkage arm and the gimbal mimic upper limb motion of the human body, provides a very similar condition to what the surgeons experience in operating room.

Embodiments of the present disclosure provide two different designs for the hand piece, called gimbal I and gimbal II, Gimbal I accommodates both single-prong and dual-prong tools, similarly, from the tool top end; such that the tool and the users hand go underneath the gimbal frame when operating the haptic device in a regular condition. The gimbal I has at least 4-DOF positional feedback, three DOFs on the gimbal joints and one DOF on the tool to measure pinching distance. Gimbal II accommodates both types of single-prong and dual-prong tools using additional holders and connectors, while possessing at least 4-DOF positional sensing feedback and at least 1-DOF force feedback.

In accordance with one embodiment, the attached surgical tools are sensorized and/or actuated. The system has at least 3 DOFs force feedback provided by at least three actuators installed on the linkage arm. In an example implementation, the surgical tool comprises a sensor, an actuator, or both. For example, the surgical tool 1-130 in the local haptic hand controller 1-100 in FIG. A can include a sensor in communication with the control system. The control system can communicate, via network, with the surgical tool at the remote robotic manipulator, either directly or via a control system at the remote location, to determine if the surgical tools at the local/master and remote/slave location match.

In an example embodiment, the system has at least 3 DOFs force feedback provided by three actuators installed on the serial linkage, or kinematic structure. The surgical tool can be actuated by a miniaturized actuator to confer one additional high-definition force feedback in the tool level to enable the user operator to feel the grasping (pinching) and dissection forces. In an embodiment, the gimbal has at least 4 DOFs of positional feedback, three out of four (roll, pitch, yaw) of which could be measured by rotary encoders, potentiometers or resolvers. The fourth DOF, tool-tip distance in the tool level, can be measured by using a Hall-effect sensor and magnet bar fixed vis-à-vis on the inner sides of the prongs.

In accordance with another embodiment of the present disclosure, different coded and exchangeable surgical tools can be applied to the gimbal, which are recognized by the control system to assess the correspondence and similarity between the tool installed on the local (master) and remote (slave) sides. Single-prong tools, e.g., suction device or dissector, are disposed onto the gimbal supported by a connector, which facilitates the tool exchange, such as a push-pull locking connector, bayonet, or threaded lock-type connector. In an embodiment, dual-prong tools, e.g., bipolar forceps or tweezers, are disposed onto the gimbal, supported by one or two miniaturized clamp(s), fixing one or two prong(s) from the lower end of the tool or clamping the tool top end using a push-pull, bayonet, or threaded lock-type connector.

Example embodiments of the present disclosure have been designed and developed based on lightweight materials—e.g., aluminum, acrylic, resin, carbon fiber—and compact elements, e.g., fasteners, bearings, couplings, and measuring instruments. To reduce the mass inertia, maximum stiffness/weight ratio and low friction joints are considered for the selected elements. In an example embodiment, heavy parts such as actuators are located as close as possible to the first (shoulder) joint and a spring-loaded belt/pulley mechanism is used to transmit the power from elbow I actuator to the elbow II axis (intersection of the arm and forearm links).

The system specifically meets the large dexterous workspace, structural link length criterion within the whole workspace, and high integrated conditioning index (ICI). Embodiments of the present disclosure specifically meet the structural link length criterion within the whole workspace, while maximum manipulability and isotropy have been considered to achieve a desirable kinematic performance. In an embodiment, the system is also equipped with a motorized dynamic counterbalance mechanism attached to the elbow support frame, which is able to rotate freely with the shoulder drum around the shoulder axis. The counterweight moves linearly back and forth towards or against the shoulder axis, synchronous with the movements of the serial linkage arm, to change the positions of the center of gravity (CG) of the entire moving parts and allows the system for further improvements in automatic gravity compensation. Moreover, the system has another mode/option for gravity compensation using weight attached to the shoulder joint. In another embodiment, the system is configured to operate in an automatic mode for gravity compensation by distributing the torque among three actuators of the serial linkage to compensate the weight of the shoulder, arm and forearm links, separately. Recognizing the attached surgical tool, the control system is configured to compensate for the weight of the tool.

Embodiments of the present disclosure concern an ergonomic system to provide comfort and flexibility for different operators and preferences. In an example embodiment, the system includes a base which supports the hand controller and allows for adjusting at least two additional degrees of freedom. Embodiments of the present disclosure introduce three base designs including: adjustable base I, adjustable base II and fixed base (stand). The adjustable base I is controlled directly by the control software connected to a graphical user interface through a touch screen or manually by force resistive sensors disposed on the base, which allow for the selection of a favorable posture in manual state.

Adjustable base II is the alternate design for the adjustable base I. In adjustable base II, the desired setting, can be adjusted manually through a joystick or remote control connected to the control software. Individual users can record preset settings and recall them when needed. This feature allows for defining a home position for the base or recalling the preset home positions. The fixed base is a simple stand useful for the users who do not need this level of adjustability/ergonomics.

In accordance with another aspect of the present disclosure; the system benefits from a modular design, capable of being taken apart quickly, by unplugging multiple connectors at each module, which facilitates the repair and maintenance of the device. In addition, the adjustable bases I and II (alternate design for adjustable base I) are detachable in the same way, as all the connectors could be disconnected and mechanical assemblies could be disassembled easily in this modular design.

In an embodiment, the base is controlled by the control system which includes a graphical user interface (GUI) and optionally a touch-screen. In an embodiment, individual users/operators can record preset settings and recall them when needed. This feature allows for defining a home position for the base or recalling the preset home position. The desired settings can be adjusted manually. Force resistive sensors disposed on the base allow for the selection of a favorable posture in manual state.

In an example embodiment, the adjustable base is powered out of a main control loop by means of gear-motors to provide at least two additional rotational/translational independent degrees of freedom to the said haptic hand-controller relative to the said reference.

In an example embodiment, the base comprises at least two degrees of freedom to adjust the height and at least one rotational angle of the haptic hand-controller to provide motion comfort for different operators regarding the said operator's body habits and preferences. In an example embodiment, the operator is able to apply preset settings or input desired settings manually on an input device, such as a touch-screen connected to the main controller, to activate actuators of the base and to change the height and the at least one rotational angle of the system to a favorable or preferred posture for the operator.

In an example embodiment, the base has a HOME position, and a control system comprises a home function whereby the operator is able to define a home position for the base or recall preset home positions.

In an example embodiment, the local haptic hand controller system comprises at least 9 degrees of freedom (DOF) and the linkage design in the kinematic structure is configured to replicate human upper limb and hand motion. In an example embodiment, a linkage arm is provided with at least three translational degrees of freedom to replicate the elbow and shoulder motions.

In an example embodiment, a serial kinematic structure is arranged between a base tilt plate and an end effector, and acts as an anthropomorphic articulated linkage and mimics the human upper limb motion intuitively. In an example embodiment, the kinematic structure provides at least three degrees of freedom including at least three translational degrees of freedom in relation to the shoulder, and at least three degrees of freedom active gravity compensation. The kinematic structure is adapted to exert forces and/or torques far at least partial compensation of gravity related forces, and/or torques acting in at least one of the three translational degrees of freedom. In an example embodiment, such gravity compensation is powered by means of actuators to power three independent freedoms of the said arm and forearm relative to the shoulder.

In an example embodiment, active gravity compensation is applied to the serial kinematic linkage structure to compensate the gravity force at least at one rotational joint including the shoulder, first elbow and second elbow.

In an example embodiment, the kinematic structure comprises a shoulder, which facilitates the flexion/extension degree of freedom for the operator for physically exchanging at least one component of a 3-dimensional force vector with an operator's hand/finger.

In an example embodiment, the linkage structure includes two links, for example an arm and a forearm, and two joints, for example first and second elbows, which facilitate both the abduction/adduction and internal/external rotational degrees of freedom for physically exchanging at least two components of a 3-dimensional force vector with an operator's hand/finger.

In an example embodiment, the kinematic structure further comprises at least three collision-free stationary actuators to provide at least three degrees of freedom, each of which pairing with a disk said drum through a capstan and backlash-free rope to generate a pull-in torque at each joint. The actuators are adapted for moving the serial linkage arm with certainly determined range of angular motion for all the relevant degrees of freedom associated to the serial linkage arm within all over the whole workspace.

Further, in an example embodiment, the system is able to generate high definition force feedback by means of at least four actuators, each meshed with a backlash-free capstan-rope transmission system to generate a pull-in torque at each joint. Such a configuration allows for enhancing the safety level during an operation.

In an example embodiment, at least one link of the entire apparatus comprises at least one long-distance spring-preloaded power transmission mechanism including belt/pulley or chain/sprocket (at least a single strand chain paired with a single roller sprocket), and other power transmitters between end joints of the associated link.

In an example embodiment, a serial linkage arm in the kinematic structure 1-120 comprises a shoulder, and first and second elbow joints having associated therewith a power transmission assembly. The power transmission assembly comprises a timing belt and two timing pulleys to transmit the torque from a motor, such as an E2-Motor, to an axle of the second elbow joint, which provides a continuous, smooth and quiet motion while it can resist the required amount of tensile force due to maximum force applied to the surgical tool.

In an example embodiment, the kinematic structure comprises a gimbal with at least three rotational degrees of freedom, for example including roll, pitch and yaw, to replicate the finger, hand and wrist motions.

In an example embodiment, the gimbal is pivotably connected to the kinematic linkage, such as to a linkage arm, and is freely able to follow the operator's wrist motion besides pinching/coagulating motions of the fingers to provide at least four degrees of freedom including: at least three translational degrees of freedom to the forearm wrist point relative to the frame affixed to the stationary frame on the tilt shaft; and at least one pinching-coagulating degree of freedom applied to the tool relative to the fixed reference frame affixed to the tool embodiment, with minimized kinematic singularities within the said virtual operating zone.

In an example embodiment comprising a hand piece, the kinematic structure includes at least two links, at least three joints and at least three measuring means, such as rotary encoders, to provide at least pronation/supination and flexion/extension degrees of freedom relative to the forearm to an operator's hand/finger.

In an example embodiment, the local surgical tool comprises a substitutable surgical tool, such that the surgical tool is removable and replaceable with a different surgical tool. In an embodiment, the surgical tool is a regular, sensorized or powered surgical tool. In different embodiments, the surgical tool is utilized in microsurgery or at least one of neurosurgical, general, orthopedic, gynecology, cardiovascular, otolaryngology, plastic, or dental surgeries.

In an example embodiment, the local surgical tool is selected from the group consisting of bipolar forceps, suction tubes, dissectors, micro scissors, tweezers, and laser. In an embodiment, the surgical tool is a connection element or end effector, physically attached and moved by the operator. The operator, or surgeon, holds and maneuvers the real surgical tools in the same way as performed in conventional surgery.

In an example embodiment, different coded and exchangeable surgical tools can be mated to the end-effector, which are recognized by the control system to assess the correspondence and similarity between the tool pairs installed on the master (local) and slave (remote) sides. In an example embodiment, the system shows a warning if the toot on the hand controller is not matched with the corresponding tool on the slave side.

In an example embodiment, the local haptic hand controller takes advantage of a self-diagnosis module that is able to detect any damaged, broken-down or out-of-order sensors by a preliminary checkup performed by the control system. Recognition of the attached surgical tool provides information for the control software to compensate for the weight of the attached surgical tool.

In an example embodiment, the local surgical tool comprises at least one position sensing and one actuation mechanism directly installed on the tool to provide the required data for at least one degree of freedom positional feedback for the prongs relative to each other (pinch/coagulation distance) and generating at least one degree of freedom haptic force feedback to sense the precise amount of pinch/coagulation force. This helps the operator, or surgeon, to avoid application of excessive force thereby improving the safety of robot-assisted surgery.

In an example embodiment, the local surgical tool comprises at least two 3-DOF position sensing hand pieces, connected to the end effector, for the right and left hands including at least one exchangeable regular or sensorized surgical tool/instrument similar to what is installed on the pairing slave operating robot.

In an example embodiment, the local surgical tool can provide at least 1-DOF additional pinch/coagulation position sensing feedback and at least 1-DOF additional pinch/coagulation haptic force feedback relative to the local end effector frame to an operators hand/finger comprising.

In an example embodiment, the local surgical tool is equipped with at least one sensor. In an example embodiment, the at least one sensor is selected from the group consisting of: magnetic sensor, hall-effect sensor, optical sensor, strain-gauge resistive sensor, piezoelectric sensor, piezo-resistive sensor, capacitive proximity sensor, and induction sensor. The sensor is configured to measure the pinching or coagulating distance between bipolar prongs and/or applied pinching/coagulating force to the tool by the operator.

In an example embodiment, the local surgical tool is equipped with at least one actuator. In an example embodiment, the at least one actuator is selected from the group consisting of: electric, electromagnetic, piezoelectric, pneumatic and hydraulic actuator, The at least one actuator is configured to generate at least 1-DOF pinching or coagulating haptic force feedback between bipolar prongs according to the real-time force applied to the tissue by the slave robot on the remote (slave) side.

In an example embodiment, the local surgical tool comprises a measuring device, such as a rotary encoder, configured to measure the roll angle.

In an example embodiment, the local surgical tool comprises a push-pull locking connector provided on at least one end point of the surgical tool, which facilitates removal and substitution, by the operator, of the surgical tool with other tools in a cart set.

In an example embodiment, the master and remote surgical tools and comprise smart sensorized forceps, and the local haptic hand controller is configured to settle the pair of smart sensorized forceps to record the positions (linear Cartesian movements), orientations (roll, pitch and yaw) and exerted interactive pinching/coagulating forces applied by the operator to distinguish or assess the surgeons' skills based on the accuracy of positioning and applied force compared to stored reference parameters.

In an example embodiment, the control system comprises a graphical user interface (GUI) configured to graphically display, and optionally animate, the speed of all actuators and angles of rotations (orientation of the base) on a display.

In an example embodiment, the control system comprises at least one human machine interface (HMI) or a computer-based touch panel, which acts as a control station for the base.

In an example embodiment, the control system comprises at least one electronic printed circuit board, one programmable chip, and one touch-based display screen connected to the circuit board for configuration/manipulation by the operator to adjust the base angles conveniently.

In an example embodiment, the HMI comprises a graphical user interface (GUI) on which two commanding modes are programmed, namely a manual mode and an automatic mode. In an example embodiment. In the manual mode, the operator pushes at least one of four force sensitive resistors (FSRs) to activate actuators of the base. The actuator speed and angle of rotation can be graphically shown on the screen, such as using gadgets. In an example embodiment, in the automatic mode, the operator instructs the parameters to be adjusted automatically by a pre-planned program, based on saved profiles for different operators, with desirable settings being capable of being saved separately for each operator.

In an example embodiment, the control system comprises at least one sound module connected to at least one speaker to audibly guide the operator through the programmed interface module, for example to guide the operator through the base setup, step by step. In an example embodiment, the control system comprises at least two push buttons for moving the entire mechanism up or down, which can be pressed by the operator to adjust the base height.

In an example embodiment, the control system comprises at least one actuator driver having at least two channels, which provide the required power for the gear motors in the base. In an example embodiment, the actuators are programmed to meet the safety requirements for medical purposes. In an example embodiment, to avoid any collision or damage, the base will bounce back gently if the operator holds the relevant push button or force sensitive resistor said FSR active to overpass the maximum angle.

In an example embodiment, a microsurgery-specific haptic hand-controller is provided for intuitive and commutative haptic interaction with an operator in a tele-operated environment. In an example embodiment, the present disclosure provides a master robot having an intuitive configuration and architecture specifically designed for robotic tele-operated surgery in a non-local environment. The master robot is configured to be paired with a slave manipulator in a way to reduce the both said training time and said effort time to perform a surgical task for surgeons of different training levels and experience.

Example embodiments of the present disclosure comprise three principle components: a base, such as an adjustable base; a serial linkage, such as a shoulder-elbow serial linkage; and a gimbal. In an example embodiment, the base joints consist of a prismatic-joint (P type), a revolute pan joint (R type), and a tilt joint (R type), referred to as PRR. The length and angle of the base joints are controlled, either manually or automatically, by the operator.

In an embodiment, the tilt counter balance weight assembly, installed an the left side of the pole 20, comprises a U-shaped sheet plate bracket 30, L-shaped sheet plate bracket 103, S-shaped sheet plate extension 29, small tilt counter weight 107 and large tilt counter weight 28. The small counter weight 107 and large counter weight 28 compensate together a large portion of the hand controller weight, which affects the tilting motion, by creating a supporting lift torque around the tilt shaft 91. The balance weights 28 and 107 are affixed to the plate link 29, for example by means of headed machined screws.

The base could be adjusted automatically or directly using a software interface, or manually by pressing one of the force sensitive resistors 80 to move it to the right, left, up, or down. In an automatic mode, the operator communicates with the hand controller via a GUI in order to adjust the base height and angles by selecting the preset settings and move the base to a favorable posture.

A hand controller, according to an embodiment of the present disclosure is provided bimanual with a right-hand device fixed to a stand, covered by plastic enclosures. In another embodiment, the hand controller is attached to any of the adjustable bases I or II covered by the enclosure.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Certain embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A local haptic hand controller for enabling an operator to remotely perform microsurgery by controlling a remote robotic manipulator, the local haptic hand controller comprising:
   a base;
   a kinematic structure in communication with the base, the kinematic structure comprising a gimbal provided as an end-effector;
   a local surgical tool provided at the gimbal and having a shape and construction substantially similar to a remote surgical tool provided at the remote robotic manipulator and with which the microsurgery is to be performed, the local surgical tool comprising a local surgical tool identifier; and
   a control system in communication with the local surgical tool and with the remote surgical tool, the control system configured to enable operation of the local haptic hand controller when a local surgical tool identifier matches a remote surgical tool identifier.

2. The local haptic hand controller of claim 1 wherein the local surgical tool comprises a local surgical tool type identifier identifying a type of surgical tool, and wherein the control system is configured to enable operation of the local haptic hand controller when the local surgical tool type identifier matches a remote surgical tool type identifier.

3. The local haptic hand controller of claim 1 wherein the local surgical tool comprises a local individual surgical tool identifier identifying a specific surgical tool, and wherein the control system is configured to enable operation of the local haptic hand controller when the local individual surgical tool identifier matches a remote individual surgical tool identifier.

4. The local haptic hand controller of claim 1 wherein the control system is configured to generate a warning when the local surgical tool identifier does not match the remote surgical tool identifier.

5. The local haptic hand controller of claim 1 wherein the control system is configured to compare the local surgical tool identifier with the remote surgical tool identifier, and to permit operation of the local haptic hand controller only when the local surgical tool identifier matches the remote surgical tool identifier.

6. The local haptic hand controller of claim 1 wherein the control system is provided in communication with, but separate from, the local haptic hand controller.

7. The local haptic hand controller of claim 1 wherein the control system comprises a local control system configured to communicate with the remote surgical tool via a remote control system associated with the remote robotic manipulator.

8. The local haptic hand controller of claim 1 further comprising a human-machine interface configured to provide an output of the control system based on a comparison of the local surgical tool identifier with the remote surgical tool identifier.

9. The local haptic hand controller of claim 1 wherein the local haptic hand controller is configured to perform self-diagnosis and to provide a result of the self-diagnosis.

10. The local haptic hand controller of claim 1 wherein the local haptic hand controller is configured to perform a diagnosis of the local haptic hand controller and to provide a result of the diagnosis.

11. The local haptic hand controller of claim 1 wherein the control system is configured to, based on the remote surgical tool identifier, provide information to the local hand controller to compensate for the weight of the remote surgical tool to reduce inertia or provide haptic force feedback.

12. The local haptic hand controller of claim 1 wherein the local surgical tool comprises at least one sensor, and wherein the local haptic hand controller comprises a self-diagnosis module configured to detect an operational status of the at least one sensor in the local surgical tool.

13. The local haptic hand controller of claim 1 wherein the local surgical tool comprises at least one sensor in communication with the control system.

14. The local haptic hand controller of claim 1 wherein the local surgical tool comprises an encoding connector in communication with the control system and configured to encode the local surgical tool with the local surgical tool identifier.

15. The local haptic hand controller of claim 14 wherein the encoding connector is configured to encode the local surgical tool with a local surgical tool type identifier.

16. The local haptic hand controller of claim 14 wherein the encoding connector is configured to encode the local surgical tool with a local individual surgical tool identifier.

17. A local haptic hand controller for enabling an operator to remotely perform microsurgery by controlling a remote robotic manipulator, the local haptic hand controller comprising:
 a base;
 a kinematic structure in communication with the base, the kinematic structure comprising a plurality of serial linkages and comprising a gimbal provided as an end-effector, the plurality of serial linkages and the gimbal cooperating, in use, to translate operator arm movement into movement of at least one of the plurality of linkages in a direction parallel to and side-by-side with the operator arm movement; and
 a control system in communication with a remote surgical tool and with a local surgical tool adapted for mating with the gimbal, the control system configured to enable operation of the local haptic hand controller when a local surgical tool identifier associated with the local surgical tool matches a remote surgical tool identifier associated with the remote surgical tool.

18. The local haptic hand controller of claim 17 wherein the operator arm movement is caused by a first serial link chain defined by the operator's arm, and the plurality of linkages comprise a second serial link chain configured to move in parallel with, and together with, the first serial link chain.

19. The local haptic hand controller of claim 17 wherein the kinematic structure comprises:
 a shoulder assembly including a rotary joint and an upper elbow joint coupled to the rotary joint;
 an upper arm pivotally connected to the shoulder assembly;
 a lower elbow joint pivotally connected to a lower end of the upper arm; and
 a forearm pivotally connected to the lower elbow joint,
 and wherein the gimbal is pivotally connected to the forearm.

20. A local haptic hand controller for enabling an operator to remotely perform fine manipulation by controlling a remote robotic manipulator, the local haptic hand controller comprising:
 a base;
 a kinematic structure in communication with the base, the kinematic structure comprising a gimbal provided as an end-effector;
 a local fine manipulation tool provided at the gimbal and having a shape and construction substantially similar to a remote fine manipulation tool provided at the remote robotic manipulator, the local fine manipulation tool comprising a local fine manipulation tool identifier; and
 a control system in communication with the local fine manipulation tool and with the remote fine manipulation tool, the control system configured to enable operation of the local haptic hand controller when a local fine manipulation tool identifier matches a remote fine manipulation tool identifier.

* * * * *